United States Patent
Sunol et al.

(10) Patent No.: US 9,863,687 B1
(45) Date of Patent: Jan. 9, 2018

(54) SELF-HEATING APPARATUS AND METHOD OF CUSTOMIZING A TIME-TEMPERATURE PROFILE THEREOF

(71) Applicants: Aydin K. Sunol, Lutz, FL (US); Sermin G. Sunol, Lutz, FL (US); Emilee Chassanne Bannister, Tampa, FL (US); Pamela Alvarez Moreno, Atlantico (CO); Kyle Louis Cogswell, Tampa, FL (US)

(72) Inventors: Aydin K. Sunol, Lutz, FL (US); Sermin G. Sunol, Lutz, FL (US); Emilee Chassanne Bannister, Tampa, FL (US); Pamela Alvarez Moreno, Atlantico (CO); Kyle Louis Cogswell, Tampa, FL (US)

(73) Assignee: University of South Florida, Tampa, FL (US)

( * ) Notice: Subject to any disclaimer, the term of this patent is extended or adjusted under 35 U.S.C. 154(b) by 243 days.

(21) Appl. No.: 14/826,416

(22) Filed: Aug. 14, 2015

Related U.S. Application Data

(60) Provisional application No. 62/037,252, filed on Aug. 14, 2014.

(51) Int. Cl.
*F24J 1/00* (2006.01)
*F25D 5/00* (2006.01)
(Continued)

(52) U.S. Cl.
CPC ............... *F25D 5/00* (2013.01); *A47J 36/28* (2013.01); *A61F 7/03* (2013.01); *F24J 1/00* (2013.01)

(58) Field of Classification Search
CPC ..... F24J 1/00; A47J 36/28; A61F 7/03; C09K 5/18; F25D 5/00; A01N 25/34; A01N 25/18; A01N 25/10
See application file for complete search history.

(56) References Cited

U.S. PATENT DOCUMENTS

| | | | |
|---|---|---|---|
| 4,751,119 A * | 6/1988 | Yukawa | A47J 36/28 126/263.08 |
| 7,754,237 B1 | 7/2010 | Borland, Jr. | |

(Continued)

FOREIGN PATENT DOCUMENTS

WO    2012006328 A1    1/2012

OTHER PUBLICATIONS

Revay et al., Evaluation of Commercial Products for Personal Protection Against Mosquitoes. Acta Tropica. 2013. vol. 125: 226-230.

(Continued)

*Primary Examiner* — Alfred Basichas
(74) *Attorney, Agent, or Firm* — Nilay J. Choksi; Smith & Hopen. P.A.

(57) ABSTRACT

Self-heating apparatus and methodology for customizing a time-temperature profile thereof. The layered apparatus includes at least a layer of phase change material and a layer of air- or oxygen-activated material. When the air- or oxygen-activated material is activated, heat is released rapidly and is absorbed by the phase change material. The phase change material then releases the absorbed heat over a long period of time. Time-temperature profiles can be adjusted based on type, amount, and configuration of phase change and air-activated materials used. The apparatus and methodology allows rapid heat-up of times of a few minutes and lasts several hours at near constant tunable temperatures.

23 Claims, 30 Drawing Sheets
(29 of 30 Drawing Sheet(s) Filed in Color)

(51) Int. Cl.
*A47J 36/28* (2006.01)
*A61F 7/03* (2006.01)

(56) References Cited

U.S. PATENT DOCUMENTS

| | | |
|---|---|---|
| 2006/0188538 A1 | 8/2006 | Emmrich et al. |
| 2009/0022767 A1 | 1/2009 | Kauffman et al. |
| 2013/0251773 A1 | 9/2013 | Galiatsatos et al. |

OTHER PUBLICATIONS

Chattopadhyay et al., Ultra Low Concentration Deltamethrin Loaded Patch Development and Evaluation of Its Repellency Against Dengue Vector Aedes (S) albopictus. Parasites & Vectors. 2013. vol. 6: 284.

\* cited by examiner

● = Temperature Thermocouples

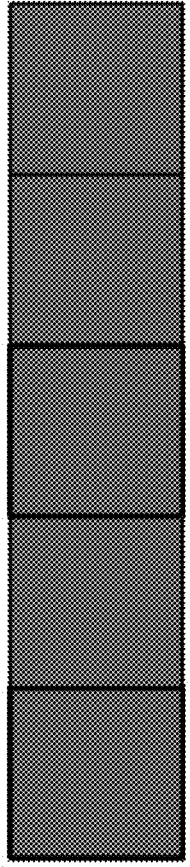
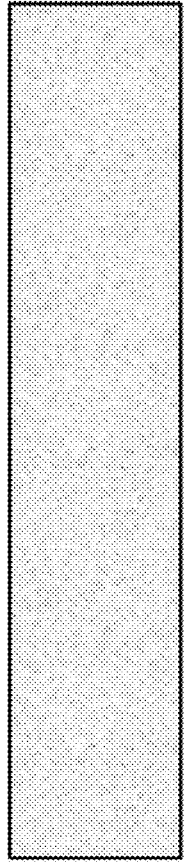
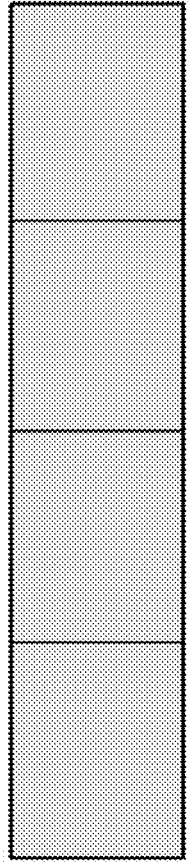
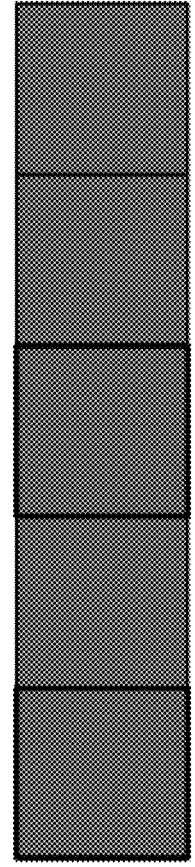
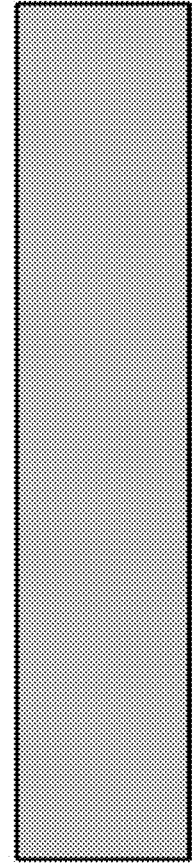
1) Top PCM Pouch
5g Lauric acid with 5 zones
2) Loose fast chemical on non-woven strip
CaO mix 1g
3) Teabag Chemical Pouch
2g CaO, 1.4 g Paraffin wax powder, 2g Mg-Fe mix, 0.35g fine Zeolite with 4 zones
4) Bottom PCM Pouch
10g Lauric acid with 5 zones
5) Insulation Layer
Neoprene
(1)  (2)  (3)  (4)  (5)
*FIG. 11*

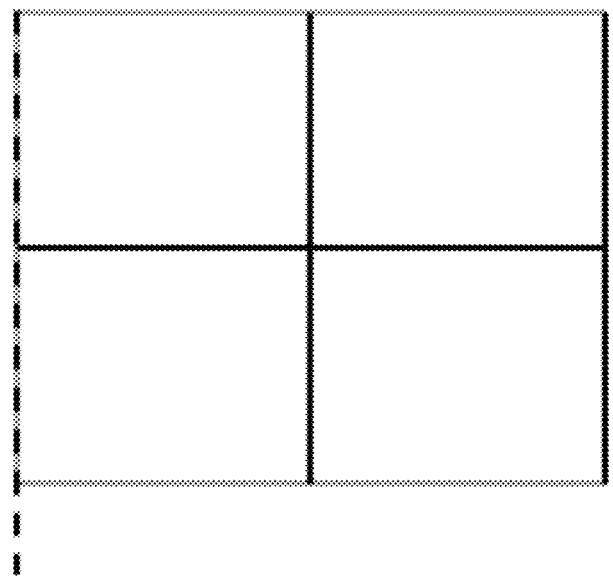
Seal _____
Fold - - - - - -
*FIG. 15A*
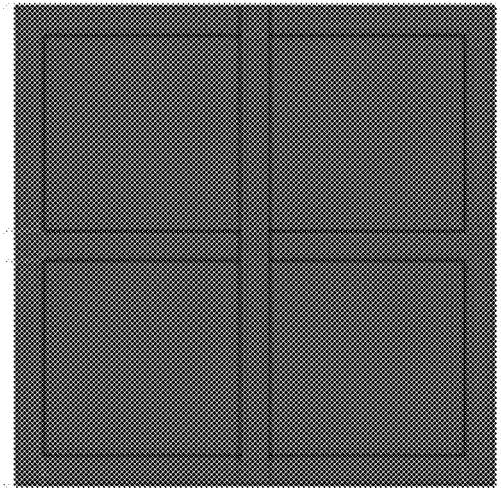
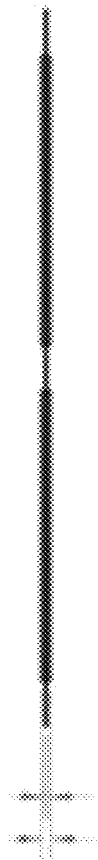
*FIG. 15B*  *FIG. 15C*

Seal ———
Fold - - - -

SELF-HEATING APPARATUS AND METHOD OF CUSTOMIZING A TIME-TEMPERATURE PROFILE THEREOF

CROSS-REFERENCE TO RELATED APPLICATIONS

This nonprovisional application is a continuation of and claims priority to U.S. Provisional Application No. 62/037,252, entitled "Self-Heating Apparatus and Methodology for Rapid and Extended Release of Low Volatile Matter", filed Aug. 14, 2014, the entirety of which is incorporated herein by reference in its entirety.

BACKGROUND OF THE INVENTION

1. Field of the Invention

This invention relates, generally, to self-heating and -cooling systems. More specifically, it relates to self-heating apparatus and methodology for attainment and modulation of customizable time-temperature profiles through chemical transformations for rapid and extended release of low volatile matter, for example for insect repellants.

2. Brief Description of the Prior Art

Self-heating and -cooling systems are well-known and utilized in development of biomedical, food, beverages, cosmetics, textiles, housing and energy applications. These systems typically involve chemical reactions that release energy (exothermic), chemical reactions that absorb energy (endothermic), or phase change. Both the amount and the rate of energy generated are key properties that vary for each chemical system. These properties must be tuned through a portfolio of methods, and the choice of materials are selected to obtain desirable time-temperature profiles for the intended applications.

One general class of applications of self-heating systems relate to extended heating at relatively constant temperature when the heat up times are short. An example will be blankets. One other general class of application of self-heating systems involves their use to enhance release profiles of beneficial active components such as medication, insect repellants, and scents. For example, the insect repellant field is often recognized by the abbreviated name of the key active ingredient utilized, DEET (N,N-diethyl-meta-toluamide). It is intended to be applied to the clothing or to a user's skin, and to provide protection against biting insects. It is estimated that 33% of the U.S. population use DEET, and each user typically purchases two units a year, providing an estimate of the annual market to be 200 million units.

The effectiveness of each unit depends on a multitude of factors, one of which is how fast the active ingredients can be dispersed around the subject (e.g., humans) or area to be protected. The rate of dispersion depends on the temperature applied to the substrate. It is also important to obtain sufficient concentration for protection and for an extended period of time. A desired time-temperature profile for many applications is shown in FIG. 1, which shows an or initial heat-up time around two (2) minutes to provide quick heating, followed by an extended constant temperature that is high enough to provide sufficient dispersion rate but low enough to economize on heat loss to surroundings and minimize harm with accidental dermal contact effects.

Current technologies fall short in providing such a temperature profile in the aforementioned general application areas including the insect repellant field. Current insect repellants must be directly applied, are activated by a heat source, are dispersed via a fan, take the form of patches, or are naturally homemade products. For example, U.S. Pat. No. 7,754,237 to Borland describes a patch to repel a subject from mosquitoes using thiamine as the repellent. U.S. Patent Application Publication No. 2013/0251773 to Galiatsatos et al. describes an insect repellent composed of several layers and a controlled insect repellent. U.S. Patent Application Publication No. 2006/0188538 to Emmrich et al. discusses an insect repellent composed of several layers and the insect repellent in the non-woven fiber layer. U.S. Patent Application Publication No. 2009/0022767 to Kauffman et al. describes a transdermally diffusible insect repellent composed of several layers. Revay et al., Evaluation of Commercial Products for Personal Protection Against Mosquitos. Acta Tropica 125 (2013): 226-230 discusses the failure of patch impregnated with repellent to repel mosquitos. Finally, Chattophadhyay et al., Ultra Low Concentration Deltamethrin Loaded Patch Development and Evaluation of Its Repellency Against Dengue Vector Aedes (S) albopictus. Parasites & Vectors 6 (2013): 284 describes a patch containing the repellent deltamethrin in demonstrating promising results in repelling mosquitoes. However, each of these publications fail to discuss a path repellant that provides an ideal, or at least more effective, time-temperature profile. For example, conventional technologies take longer than two (2) minutes to initiate (heat to at least 40° C.) and maintain the desired temperature for only about thirty (30) minutes. This can be contrasted to a desirable time-temperature profile in FIG. 1. These conventional technologies typically use an air-activated iron reaction or supersaturated metal salts.

Accordingly, what is needed is a self-heating method and apparatus that can obtain a more effective and tunable time-temperature profile. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved self-heating apparatus and method of use thereof is now met by a new, useful, and nonobvious invention.

In an embodiment, the current invention is a self-heating, layered assembly. The assembly includes a first layer (e.g., at least 4 pouches) formed of phase change material (PCM; e.g., lauric acid, sodium acetate, etc.) layered substantially adjacent to a second layer (e.g., at least 6 pouches) formed of air-activated material (AAM; activated by the presence of oxygen and releases heat upon activation; e.g., calcium oxide, paraffin, a magnesium-iron mix, zeolite, etc.). A top film forms the top side of the layered assembly above the first and second layers. The PCM acts as both a heat sink and a heat source. As a heat sink, the PCM absorbs heat from the AAM when the AAM is activated. As a heat source, the PCM releases the absorbed heat slowly over time.

When the bottom side of the layered assembly is a contact surface (e.g., with a body or other mass), the top side of the layered assembly should be exposed to the external environment. In this case, the PCM layer would be positioned below the AAM layer, so that the AAM is exposed to the air/external environment. Alternatively, when the PCM layer is disposed below the AAM layer (even in cases when the bottom side is not a contact surface), a third layer formed of AAM material can be positioned substantially adjacent to and below the PCM layer (the AAM layers sandwich the PCM layer), such that either or both AAM layers are exposed to the external environment.

In an alternative embodiment, the first layer of PCM can be disposed above the second layer of AAM. In this case, a third layer formed of additional PCM can be disposed substantially adjacent to and below the AAM layer. In other words, the PCM layers sandwich the AAM layer.

Optionally, a thin nonwoven layer may be disposed between the AAM and the PCM and include calcium oxide in its composition. In another embodiment, a water pouch may be disposed above the PCM and AAM layers and form at least a portion of the top side of the layered assembly. In yet another embodiment, insulation may be disposed substantially around the PCM and AAM layers to modulate temperature and release heat over time.

The layered assembly may be configured to reach a temperature of over about 40° C. within about thirty (30) seconds of activation of the AAM. Further, the PCM can release the heat it absorbed for over about six (6) hours while maintaining the temperature over about 40° C.

In certain embodiments, the PCM and at least some of the AAM can be encapsulated.

In another embodiment, the current invention may include any one or more of the foregoing features and advantages described.

In a separate embodiment, the current invention is a method of manufacturing a self-heating, layered assembly for customizing a time-temperature profile for the layered assembly. A layer of PCM and a layer of AAM are provided and layered on one another within the layered assembly. The AAM layer is positioned above or below the PCM layer depending on access of the top side and bottom side of the assembly to the external environment, as the PCM layer needs access to the air/external environment. A film is disposed substantially adjacent to the AAM layer to provide a permeable barrier between the AAM layer and the external environment.

The AAM layer may be sandwiched between two PCM layers, or alternatively, the PCM layer may be sandwiched between two AAM layers.

Optionally, a thin nonwoven layer may be disposed between the AAM and the PCM and include calcium oxide in its composition. In another embodiment, a water pouch may be disposed above the PCM and AAM layers and form at least a portion of the top side of the layered assembly. In yet another embodiment, insulation may be disposed substantially around the PCM and AAM layers to modulate temperature and release heat over time.

The layered assembly may be configured to reach a temperature of over about 40° C. within about thirty (30) seconds of activation of the AAM. Further, the PCM can release the heat it absorbed for over about six (6) hours while maintaining the temperature over about 40° C.

In certain embodiments, the PCM and at least some of the AAM can be encapsulated.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 11 depicts components of a layered patch according to an embodiment of the current invention.

FIG. 15A is a schematic of PCM pouches that can be disposed in the patch assembly of FIGS. 13A-13C.

FIG. 15B is a top view of the PCM pouches of FIG. 15A.

FIG. 15C is a side view of the PCM pouches of FIG. 15A.

DETAILED DESCRIPTION OF THE PREFERRED EMBODIMENT

Figure 1:
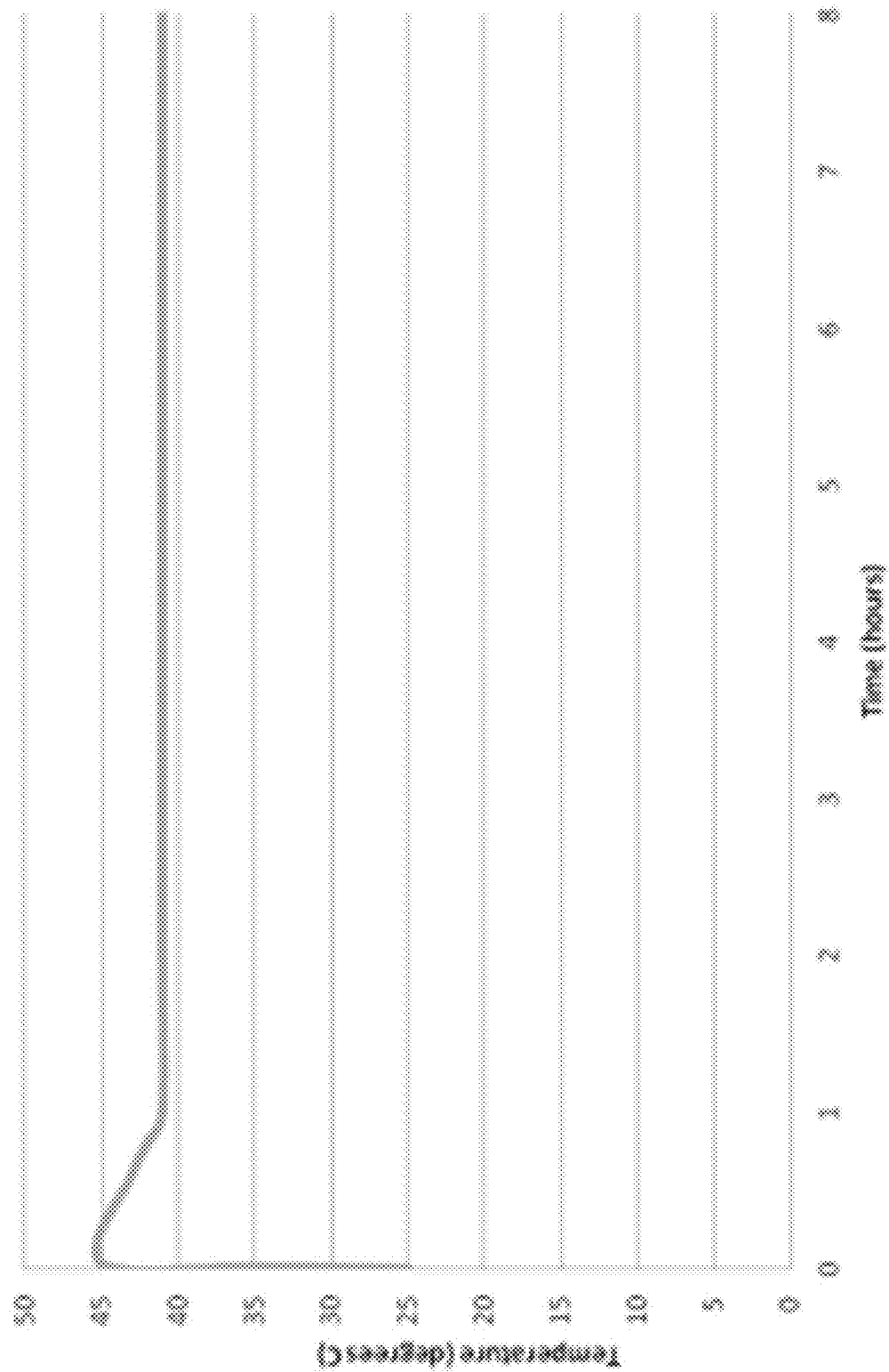
FIG. 1 is a graphical illustration of a desirable time-temperature profile.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

It is an object of the current invention to provide a self-heating apparatus that can provide heat rapidly, control temperature, and allow release of heat for a long period of time. Typically with self-heating apparatuses, such as hand or foot warmers for example, heat is lost very quickly to the surrounding environment. It is an object of the current invention to channel this heat, store it, and release it over a period of time.

Generally, the current invention uses a unique combination of phase change material (PCM; e.g., lauric acid, sodium acetate, etc.) and air-activated reactive material (AARM) to achieve this goal with unexpected success, such that the results obtained were far greater than just the sum of the PCM and AARM. When the AARM was activated by exposure to air or heat, thus releasing heat, the PCM was capable of absorbing and storing that heat and releasing that heat into the external environment. The PCM, therefore, acts as both a heat sink (absorbing heat) and a heat source (releasing heat).

The PCM can be any suitable material known in the art. For example, PCM can be organic, such as paraffins and lauric acid, or can be salt hydrates, such as sodium acetate. The organic PCMs require an external heat source, such as what comes from the internal reaction. The salt hydrates are supercooled substances, and once nucleated they provide heat. The current invention also contemplates eutectic mixtures to be used as PCM in application. The PCM can also be in macro, micro, or molecular level encapsulated.

The AARM can also be any suitable air-activated material known in the art. For example, iron or zinc can be used. These systems use salts, such as sodium chloride or potassium chloride, as a catalyst. They typically can have activated carbon or vermiculite as insulating/adsorbing porous material as well.

The phase change materials of interest are ones where the phase change occurs between 35 to 65 degrees centigrade.

Two main factors—how quickly a high temperature can be obtained and how long heat can be released, collectively the time-temperature profile—are affected by the specific type of material included in the PCM and AARM and how the PCM and AARM are configured/layered on top of each other. For example, the heating mechanism can be prolonged when alternating the PCM and AARM in layers, thus also alternating heat source and heat sink. As another example, reaction rate increases (thus decreasing the length of time of heat release) when working at higher temperatures. As a further example, if sodium acetate is used as the PCM (note that PCMs function at a constant temperature), then the temperature can be controlled at around 55° C., whereas other PCMs would have different temperatures.

In exemplary applications, the current invention can be used to release scents, release pharmaceuticals to the body using a patch design if the delivery is coupled with self-heating mechanisms, disposed seats in a venue (e.g., stadium), positioned in blankets, disperse fragrances using heat, etc. Low volatile materials can be released outside (ambient) or to the substance (e.g., body) where there is contact (for example a patch contacting a body) or where the device is self-standing (for example in a stadium seat or blanket).

Different configurations of the layers enable modulation of performance of the novel apparatus. In each case, though, the PCM becomes a heat sink and a heat source within the application, when combined with the AARM. This also avoids hot spots, which occurs in conventional applications when the reaction is taking place too fast, the heat cannot be removed, and it burns. In the current invention, the PCM can absorb the heat and then release the heat over time, thus avoiding hot spots.

Within the apparatus, at least one of the layers would include AARM, preferably with the PCM disposed thereunder so that the AARM has sufficient access to air for activation. There can be a tradeoff, however, between access to air for the AARM and maintenance of a constant temperature, which is facilitated by use of the PCM. If the PCM is at the bottom next to the insulation, the PCM initially provides the temperature to heat the AARM, so the reactions take place more quickly. However, if the PCM is on top, then there may be some difficulty getting the AARM actually activated due to less access to the outside air, though temperature would stay more uniform.

In an embodiment, the invention is related to customizable time-temperature profiles for self-heating apparatuses. Rapid and intense release of low volatile immobilized matter from a film that is in contact with the heat source is achieved for an extended period as the result of such temperature-time profiles. Generally, the invention contains the following elements: PCM or an element containing PCM, insulating material, film with immobilized volatile material, reactive mix with all components with the exception of air, and heating activation mechanisms.

In an embodiment, the current invention is related to attainment of customized time-temperature profiles, such as the one shown in FIG. 1. The profile is aimed at extended, intense, and rapid release of low volatile immobilized matter from a film that is in contact with the heat source. The release rate is modulated as a result of such time-temperature profiles. In certain embodiments, the demonstrated time-temperature profiles are obtained through a synergistic combination of salt hydrate-based phase change material and air-activated reactions.

In certain embodiments, such as the following non-limiting examples, the current invention utilizes sodium acetate as the phase change material and air-iron "rusting reaction" element providing the exothermic heat. The PCM-containing element provides rapid heating of the product elements upon activation. The air-iron rusting reaction element provides extended modulated heating through a separate activation mechanism. Both heat sources also act as heat sinks, thus minimizing heat loss, extending heating, and modulating heat rate throughout the product performance period. The combined effects enable extended heating and heat modulation throughout the performance period of the invention.

In an embodiment, the current invention is a synergistic combination of different methods of obtaining temperature profiles and their integration with initiation.

It is contemplated herein that the heating element includes combined use of salt hydrates with reactive systems, thus providing enhanced heat generation rates, temperature control, and increased total heat generation. Further, seeding mechanisms can be used for the initiation of phase change crystallization system.

Exemplary applications of the current invention include, but are not limited to, release of insect repellants, release of scents or aromas embedded in matrix (see PCT App. No. PCT/US/2011/043042 for example for the general concept), hand and foot warmers, food heaters, drug delivery via patches, topical heat applications such as for relieving pain (similar to the effects of ICYHOT but without being an ointment) or cough suppression (similar to the effects of VICKS VAPORUB), release of oils, use with tea light candles, use with electric plugins for heat, among other suitable applications.

Several subsystems are contemplated herein for integration into an efficient design.

Phase Change Material

In an embodiment, the phase change material may be a salt hydrate that releases energy upon crystallization. The reaction below is for a sodium acetate system:

$$NaC_2H_3O_3 3H_2O(l) \leftrightarrow NaC_2H_3O_3 3H_2O(s) + heat$$

A supersaturated sodium acetate solution may include, for example, four (4) mL distilled water and 28 g of sodium acetate trihydrate. As will become clearer as this specification continues, the system containing the sodium acetate trihydrate may be activated by mechanical energy (e.g., metal disk) and/or seed crystals.

Phase change materials provide rapid heating, and the resulting systems are reusable. However, they have relatively low energy density. This can be illustrated through reaction calorimetry as shown in the FIG. 2. As seen, sodium acetate can provide rapid heating but has lower energy density.

Phase Change Material Enclosing System

The enclosing element includes phase change material and either a metal disc for initiation of crystallization or a compartmental system with a seed crystallization. This subsystem will serve as a heat sink, as well as a source, depending on whether it is heated with auxiliary heat source or not. In the following set of depictions, the system is used as the heat source.

Figure 2:
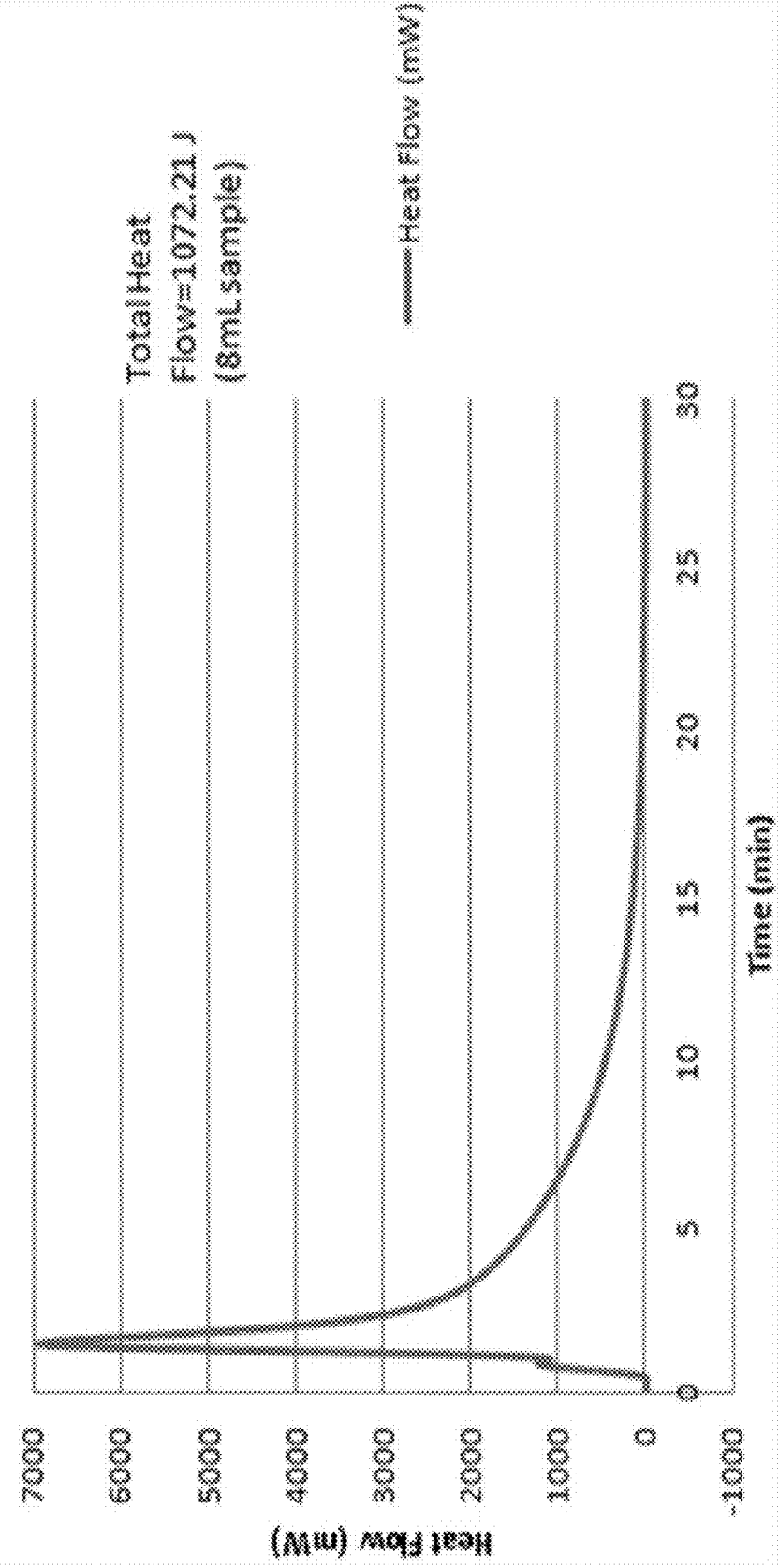
FIG. 2 is a graphical illustration of a sodium acetate heat time profile.
Figure 3:
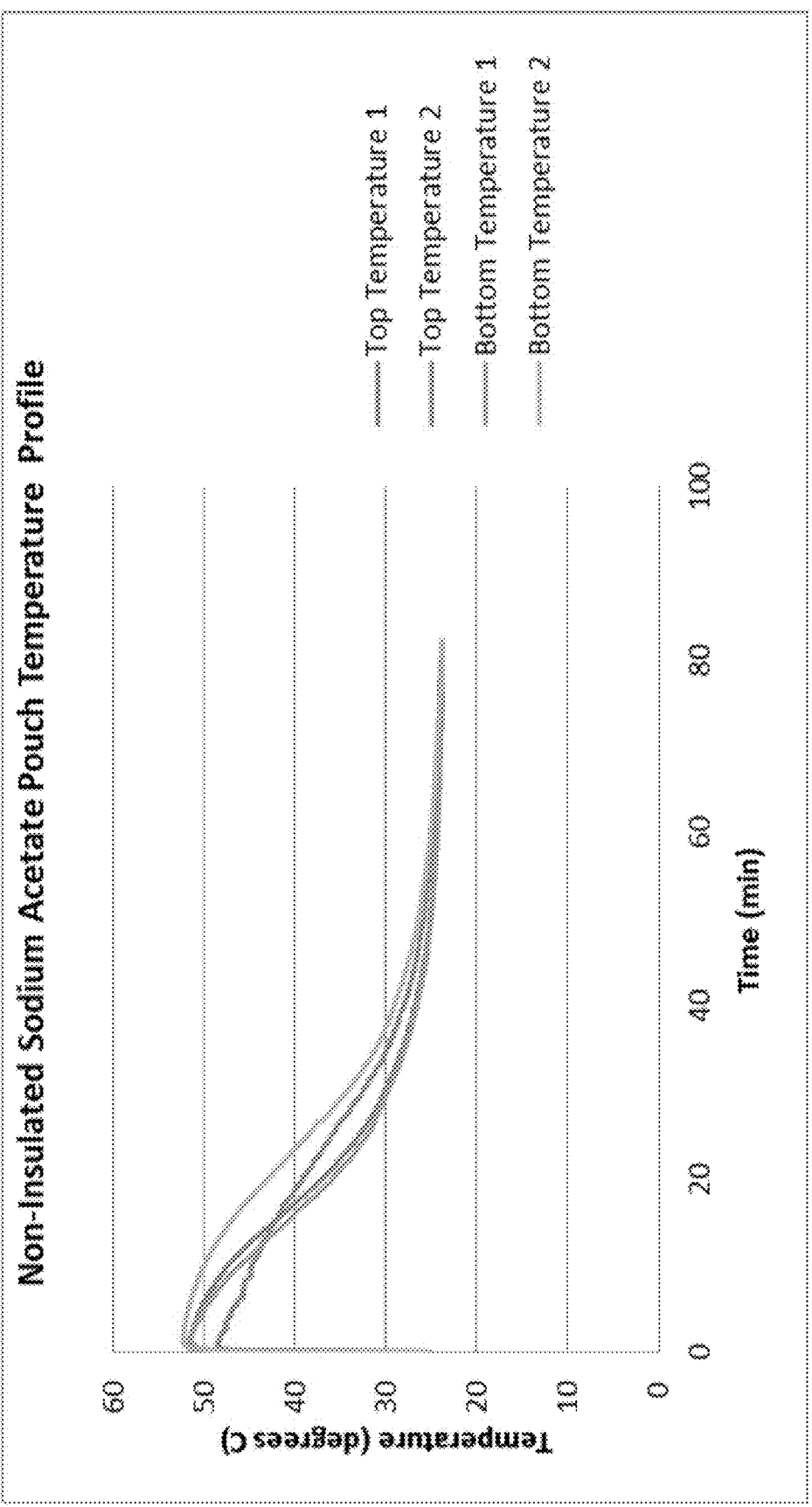
FIG. 3 is a graphical illustration of a non-insulated pouch time-temperature profile.
Figure 4:
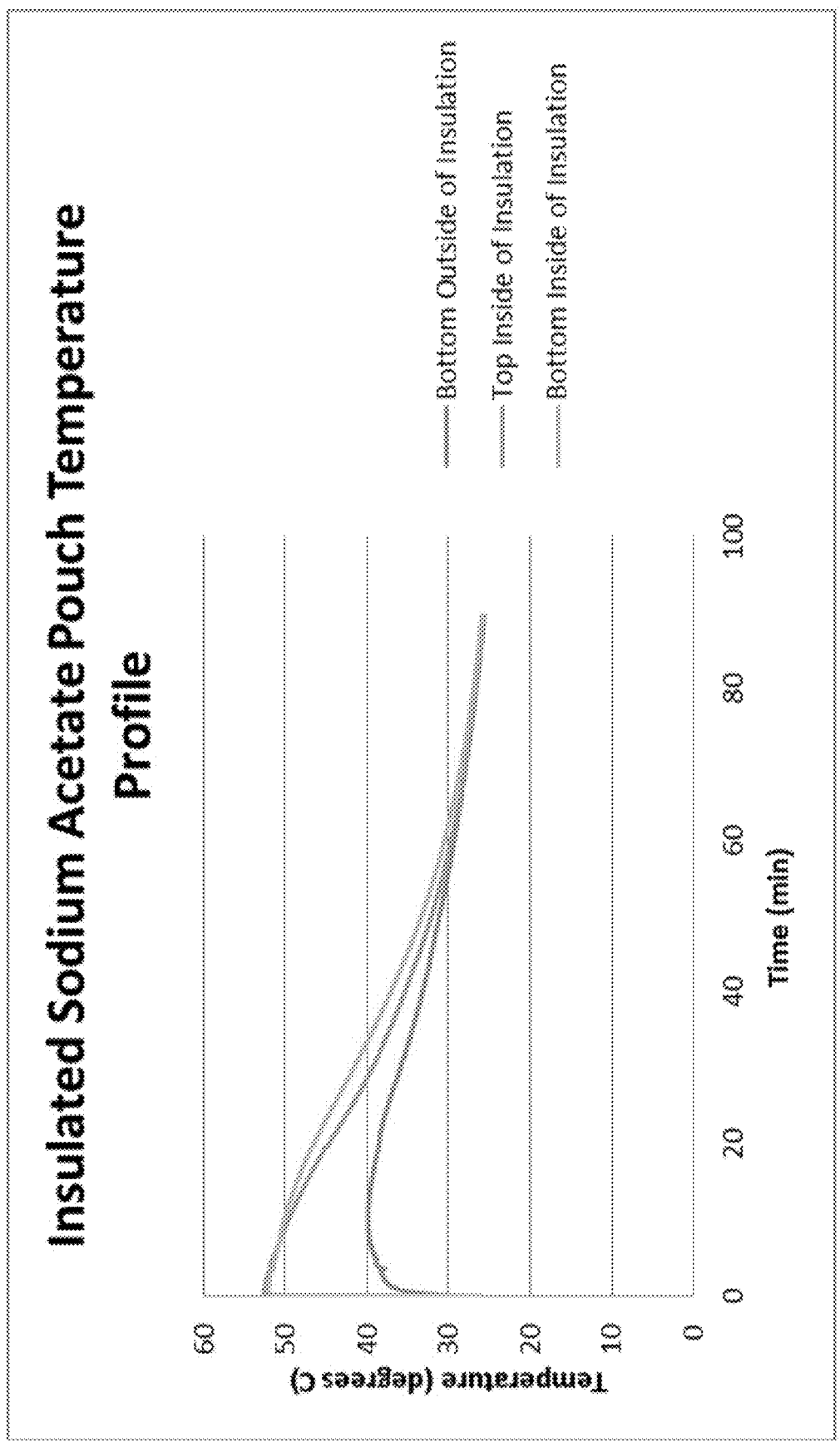
FIG. 4 is a graphical illustration of an insulated PCM time-temperature profile.

While FIG. 2 provides rapid heating data obtained through calorimetry, it is contemplated herein that testing can be accomplished with insulation, as shown in FIG. 3, and without insulation, as shown in FIG. 4.

As can be seen from FIGS. 2 and 3, heat generation using sodium acetate is nearly instantaneous. The amount of sodium acetate trihydrate used was 28 grams, along with four (4) mL distilled water, mixed and cooled. The test was initiated with a rough room temperature needle. Within sixteen (16) to nineteen (19) minutes, the top temperature was reduced below the desired 40° C. The energy per gram of sodium acetate (NaOAc) can be calculated as follows:

Sample: 2 mL H$_2$O, 14 g NaOAc $$\frac{14 \text{ g NaAc}}{1.28 \frac{g}{mL}} = 10.94 \text{ mL NaOAc}$$

2 mL H$_2$O+HO 10.94 mL NaOAc=12.94 mL soln $$\frac{14 \text{ g NaOAc}}{12.94 \text{ mL } soln} = 1.08 \frac{\text{g NaOAc}}{\text{mL } soln}$$

$$8 \text{ mL sample} * 1.08 \frac{\text{g NaOAc}}{\text{mL } soln} \approx 8.64 \text{ g NaOAc}$$

$$\frac{1072.21 \text{ J}}{8.64 \text{ g NaOAc}} = 124.10 \frac{\text{J}}{\text{g NaOAc}}$$

*Assuming volumes are additive, substances have similar densities, the mixed solution estimated should not be vastly different than the actual solution density*

FIG. 4 illustrates the benefit of using insulation. Although the system is not optimized, it can be seen that the same 40° C. mark can be retained for at least about thirty (30) minutes (bottom outside of insulation for 33.7 minutes and top inside of insulation for 28.9 minutes).

As the phase change material is changed, the maximum temperature that can be obtained will change also. The amount of heat released by salt hydrates do not change significantly on a per-gram basis. The crystallization temperature that can be obtained can be tailored somewhat by using mixtures as well.

It is an object of certain embodiments of the current invention to heat a predefined area to 40° C. or above within two (2) minutes and maintain the desired temperature for at least about two (2) hours to about four (4) or six (6) hours.

Reactive Mix (AARM)

It is contemplated herein that a range of reacting systems can be used. These are typically either air-based exothermic reactions or water-based exothermic reactions, both of which are contemplated by the current invention. Though water-based reactions can be used, the following embodiments of the current invention with be described based on the air-based reaction.

Iron-rusting reactions (iron+water+air=heat and iron (III) oxide) can be used herein. The reaction mix used includes iron, water, air (primary source of oxygen), porous adsorbent (e.g., vermiculite), and salt (e.g., sodium chloride). This system can serve as a heat sink, as well as a heat source. This reaction system provides relatively constant temperature release for an extended time with a high-energy density. However, it takes quite a bit of time to reach the desired temperature and also requires an air source.

Figure 5:
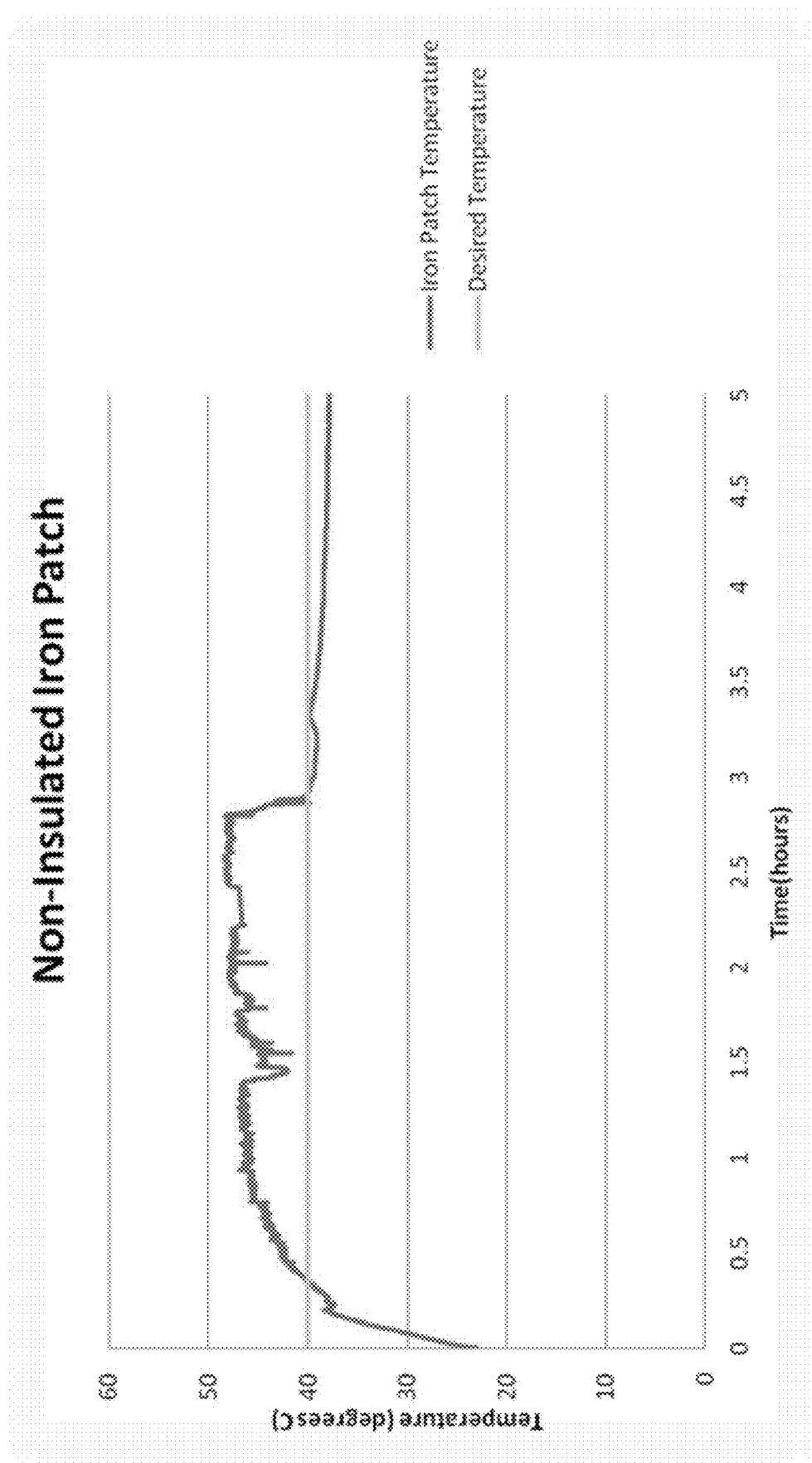
FIG. 5 is a graphical illustration of a time-temperature profile for the reactive system.

The reaction mechanism is shown below, and the time-temperature profile is illustrated in FIG. 5 for a non-insulated case (e.g., GRABBER Hand Warmers):

Overall: $4Fe+3O_2 \rightarrow 2Fe_2O_3 + \text{heat}$

Breakdown: $Fe(s) \rightarrow +Fe^{2+}(aq)+2e^-$ $O_2(g)+2H_2O(l)+4e^- \rightarrow 4OH^-(aq)$ $Fe^{2+}(aq)+2OH^-(aq) \rightarrow Fe(OH)_2(s)$ $4Fe(OH)_2(s)+O_2(g) \rightarrow 2Fe_2O_3 \cdot H_2O(s)+2H_2O(l)$ Conventional hand warmers typically are one-time use, typically including AARMs only without PCM, or are multiple use, typically including PCM (sodium acetate) packets without AARM (these are supersaturated solutions that are unstable, where when a user rubs it, it is nucleated and crystallizes and releases heat). It is contemplated herein that the current invention includes embodiments that can be one-time use or can be configured for multiple use. For one-time use, the AARM in the apparatus is depleted after use, but for multiple use, the AARM can be replaced within the apparatus. In each case, the PCM can be embedded into the apparatus permanently.

Reactive Mix Enclosing System

The reactive mix should be free of air (oxygen) until activation. Upon activation, there should be sufficient oxygen supply for a sustained reaction.

Insulating Layers

Insulating layers minimize heat loss, as well as assist in channeling the heat source through the low volatile material release zone.

Film with the Immobilized Low Volatile Material

This film can contain the low volatile material that will be released upon release activation.

Example 1

Certain embodiments of the current invention are applicable to many different physical design and application areas; the following example employs a patch design but is not intended to limit the scope of the invention in any way.

Figure 6:
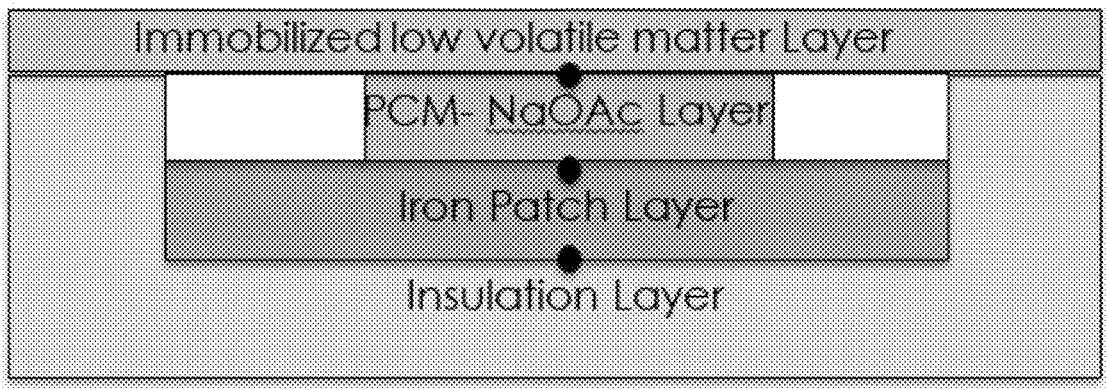
FIG. 6 depicts a design, according to an embodiment of the current invention, with the PCM layer at the top (G3001).
Figure 7:
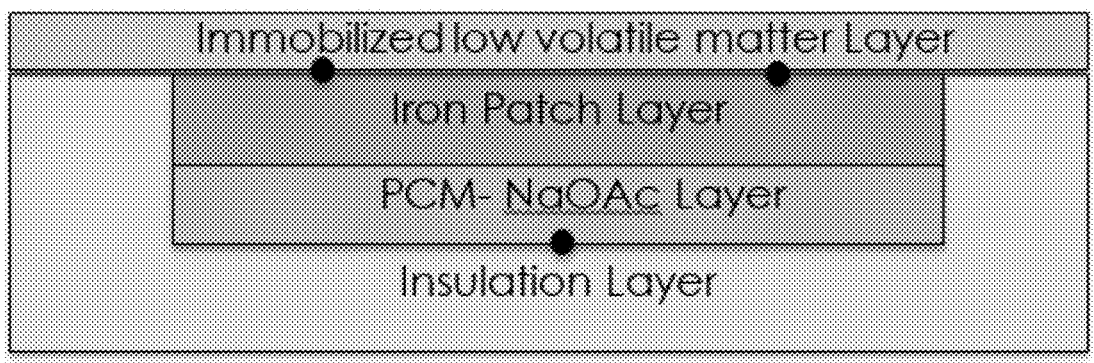
FIG. 7 depicts a design, according to an embodiment of the current invention, with the reactive mix at the top (G3002).
Figure 8:
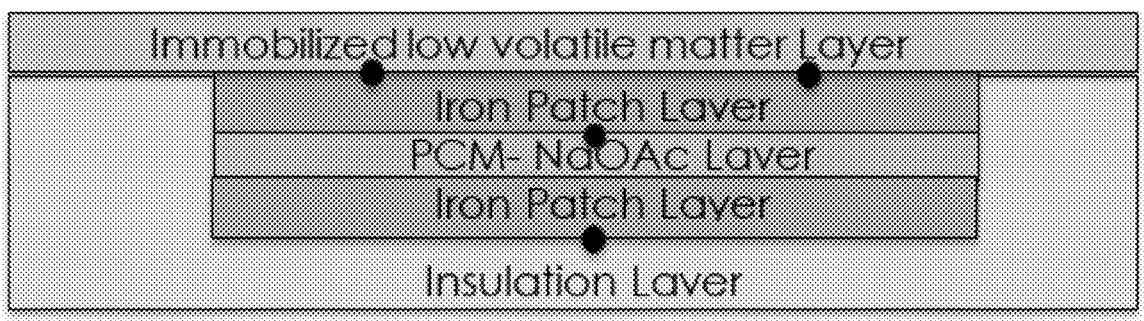
FIG. 8 depicts a design, according to an embodiment of the current invention, with a sandwiched PCM layer (G3003).

The patch top surface (immobilized low volatile matter layer) is initially sealed but, upon activation, is open to air. Three (3) different designs/embodiments are described herein, as seen in FIGS. 6-8. The first design (FIG. 6) employs the PCM layer as the top heating layer, followed by the reaction mix therebelow; the second design (FIG. 7) uses the reaction mix as the top layer, followed by the PCM layer therebelow; and the third design (FIG. 8) sandwiches the PCM layer between two reaction mix layers. In each design, an optional insulation layer was positioned beneath and lateral to the PCM and reaction mix layers. To record temperature within each design in real-time, each design included temperature probes indicated as bold dots in FIGS. 6-8.

The time-temperature profiles generated for the designs illustrate the synergistic benefit of coupling reactions and phase change materials. The results for FIG. 6 (first design) are not shown herein since it did not have sufficient allowance for air excess to the reactive mix.

Figure 9:
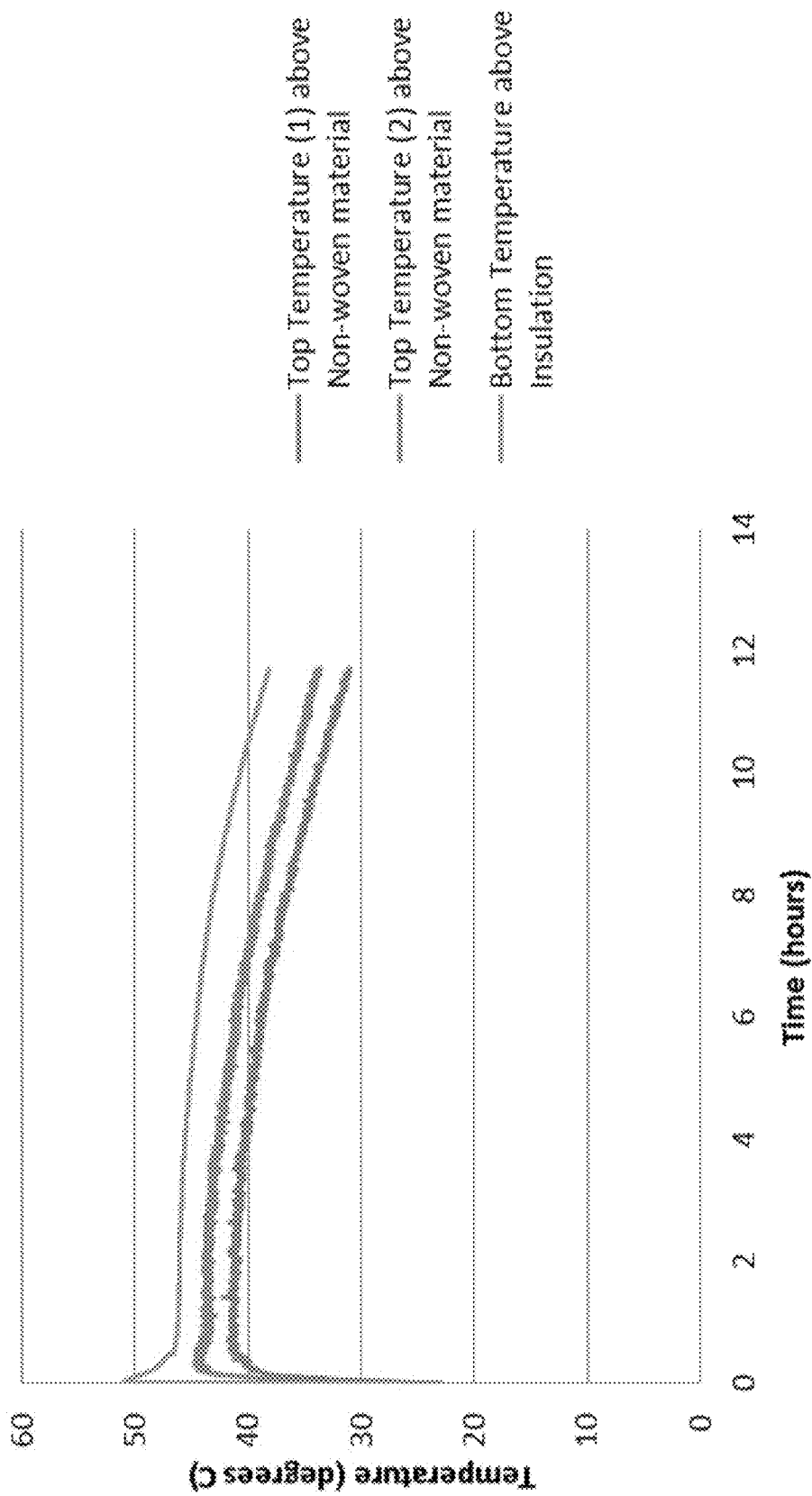
FIG. 9 is a graphical illustration of a time-temperature profile of patches with the reactive layer at the top (see FIG. 7).

FIG. 9, showing results of the embodiment of FIG. 7, illustrates that heat-up times of about 30 seconds can be obtained to reach 40° C., and this temperature can be sustained for about seven (7) hours.

The embodiment of FIG. 7 can be further optimized by adjusting the PCM to the reactive mix ratio. The PCM reaction profile suggests that the PCM may not be fully crystallizing, but rather absorbing and releasing heat based on heat capacity. The optimal ratio of PCM and reactive mix (AARM) depends on the energy required/released for phase material in the case of phase change material and the energy generated by the reaction mix within a time period such as five minutes for the reaction mix. The PCM to reactive mix ratio depends on this. Sufficient heat is needed to cause the phase change in the PCM.

The two temperature probes between the patch top surface and the iron patch layer provided different temperature profiles at their respective locations. These temperature profiles can be further optimized by avoiding local hot spots as can be seen from the deviation shown in FIG. 9. Hot spots can be detected by measuring temperature at different locations. This can dictate adjustment of the reaction mix, phase change material mix and the amount of insulation used.

The embodiment of FIG. 8 was formed for the objective of extending the total heat release, as can be seen from FIG.

10. Within minutes, goal temperatures can be reached and maintained within the system for about six (6) hours and can stay over 45° C. for over twelve (12) hours. It should be noted that the addition of the two (2) iron patch layers (AARM) results in the amount of energy contained in the corresponding reactions being 10-20 times the amount of energy that could be released by the same amount of PCM. Thus, to provide the same amount of heat as the AARM, many more PCM pouches would be needed. This shows the necessity of the AARM in the current apparatus. On the other hand, if only AARM is included in the layered apparatus and no PCM is present, then the reactions would take place and the heat would be dissipated into the external environment very quickly, as is the case with many conventional self-heating apparatuses. This shows the necessity of the PCM in the current apparatus.

It should also be noted that the optional lower iron patch layer in FIG. 8 can produce oxygen in case there is no access or limited access to air. Oxygen can be provided from the surrounding environment (air) or can be provided from another mechanism, such as the lower reactive layer here (the reactive mix may have a component that can provide oxygen to for the reaction). Examples of components in the reactive mix that can provide the oxygen include, but are not limited to, hydrogen peroxide or oxygen in micro-capsule.

Figure 10:
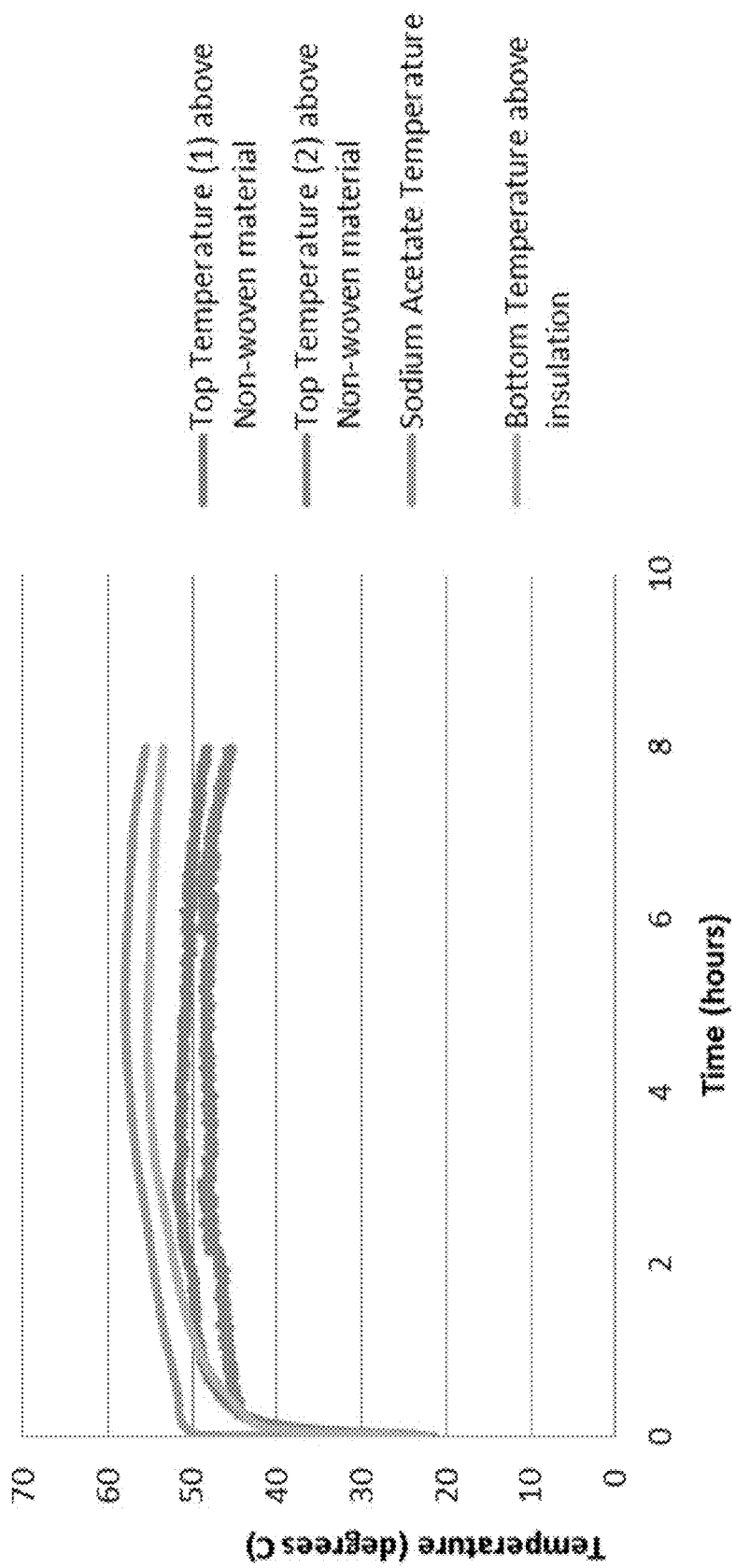
FIG. 10 is a graphical illustration of a time-temperature profile of patches with the sandwiched PCM layer (see FIG. 8).

The total duration of heat release for the embodiment of FIG. 8 was determined to be a function of the amount of reaction mix used, which is twice the amount used in the embodiment of FIG. 7. However, the rate of initial heating is seen to be lower than the FIG. 7 embodiment. This may occur, in part, because the lower PCM/reactive mix implies less heating of the reactive mix by the PCM. Lower initial temperatures for reaction imply lower initial reaction rates. Higher PCM temperatures, as seen in the FIG. 10, illustrate the PCM effectively changing phase and being heated beyond crystallization temperature, implying that it serves as the heat sink.

The current invention was seen to experience unexpected results, beyond just the sum of the combination of AARMs and PCMs. When combined, the two materials were seen to have a synergistic effect with one another. First, when the AARM was activated by air/oxygen, the apparatus was capable of achieving a high temperature very quickly. PCMs are known to get hot more easily and quickly, but when the AARM was activated, the entire apparatus showed characteristics of the PCM, namely the entire apparatus got hot very quickly. The PCM unexpectedly helped the AARM and surrounding air get hotter quickly also.

Further, it was unexpected for the apparatus to not experience hot spots when the apparatus reached a high temperature so rapidly. The PCM was seen to be able to absorb the heat and release that heat slowly but effectively over a longer period of time. In other words, the heat had a place to go before being released back into the surrounding environment, thus avoiding the hot spots.

It was additionally surprising to see the alternation of the PCM between heat source and heat sink. The PCM was initially included just to keep a constant temperature, but the PCM was then seen to be able absorb heat and get hot very quickly, followed by releasing heat slowly. This allowed for controlled modulation, rather than temperature peaks and valleys, and it also allowed for controlled progression of temperature through the self-heating and cooling process.

Example 2

Figure 12:
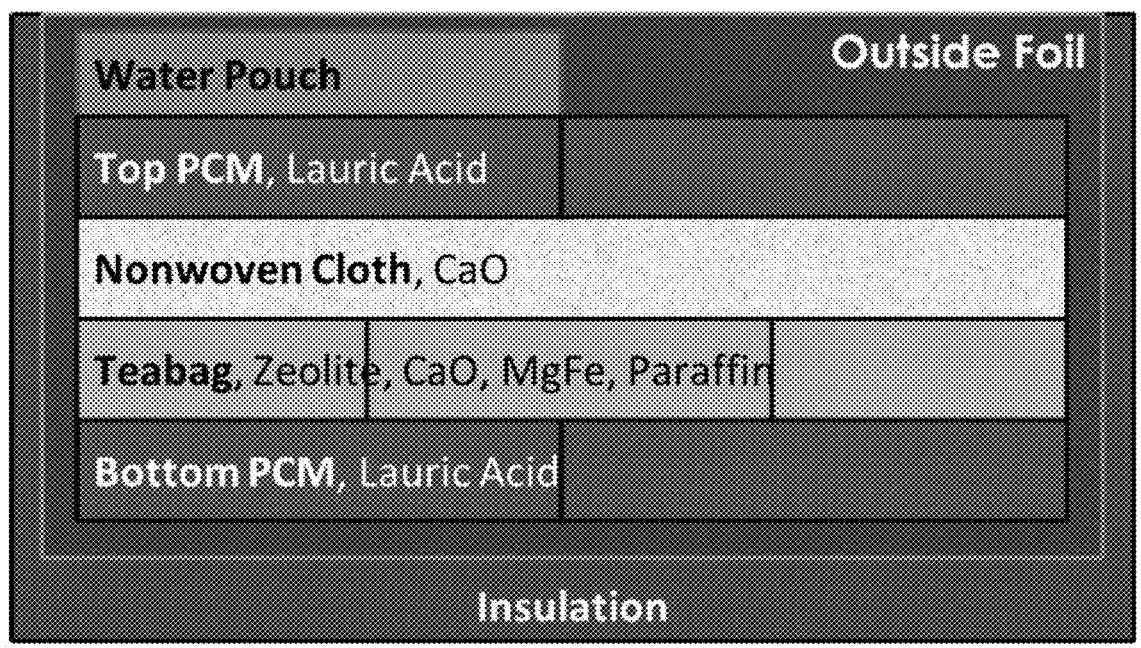
FIG. 12 is a schematic of a layered patch according to an embodiment of the current invention.
Figure 13A:
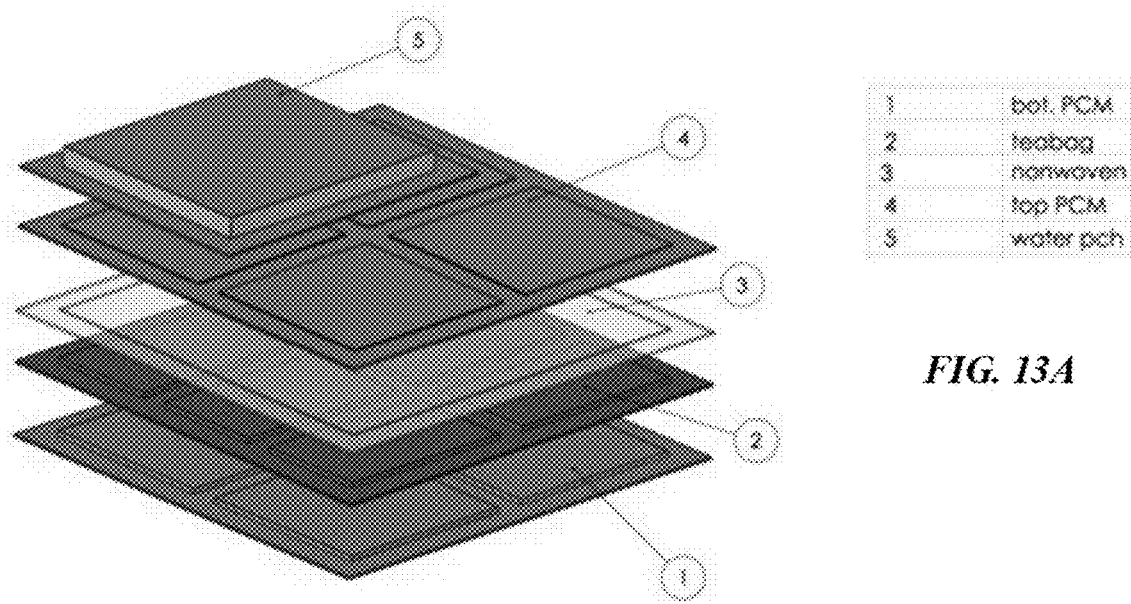
FIG. 13A is a perspective exploded view of a patch assembly according to an embodiment of the current invention.
Figure 13B:
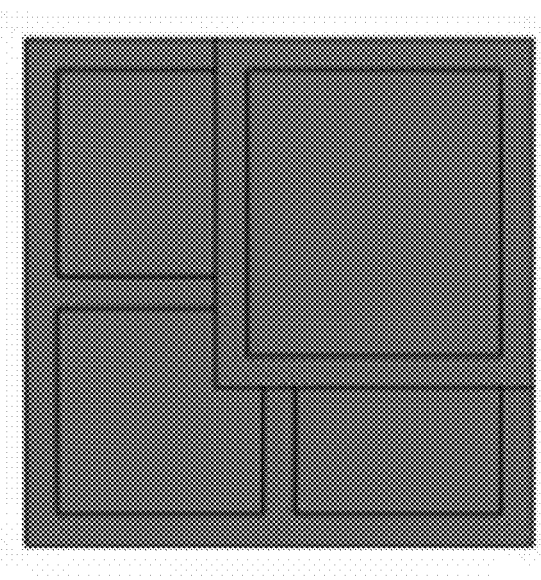
FIG. 13B is a top exploded view of the patch assembly of FIG. 13A.
Figure 13C:
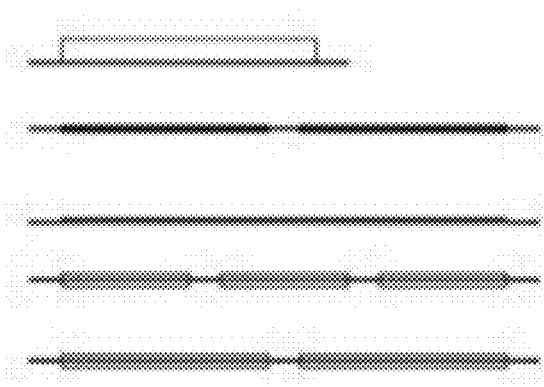
FIG. 13C is a side exploded view of the patch assembly of FIG. 13A.

An embodiment of the current invention can be seen in FIGS. 11-18. FIGS. 11 and 12 are schematics of the layered device. FIGS. 13A-17 show the layered device in exploded view, along with the components of the device. Specifically, FIG. 13A is an exploded perspective view of the layered assembly, FIG. 13B is a top view thereof, and FIG. 13C is an exploded side view thereof. The first (bottommost) layer is a bottom PCM layer with four (4) chambers. The second layer is the teabag pouch (AARM layer) with six (6) chambers. The third layer is the nonwoven cloth. The fourth layer is the top PCM layer with four (4) chambers. Any number of PCM and AARM chambers are contemplated by the current invention. PCM and AARM tend to clump, so in an embodiment, they were broken into smaller chambers, though an excessive number of chambers is impractical for manufacture. The fifth (topmost) layer is a water pouch that has dimensions smaller than the other layers of the assembly. It should be noted that insulation can optionally surround the bottom and sides of the assembly (all surfaces but the top surface). Additionally, an outer foil can also optionally surround the entirety of the layered assembly, as can be seen in FIG. 12.

Figure 14A:
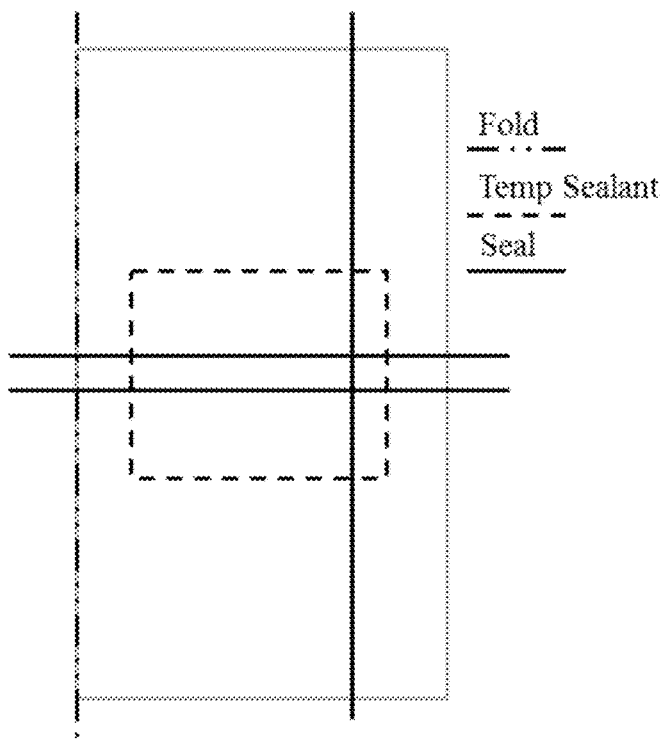
FIG. 14A is a schematic of a water pouch that can be disposed in the patch assembly of FIGS. 13A-13C.
Figure 14B:
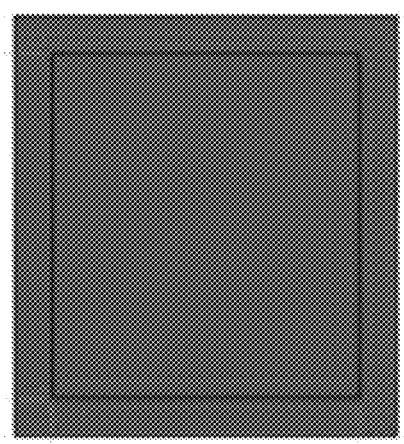
FIG. 14B is a top view of the water pouch of FIG. 14A.
Figure 14C:
FIG. 14C is a side view of the water pouch of FIG. 14A.

FIG. 14A is a schematic of the water pouch, FIG. 14B is a top view thereof, and FIG. 14C is a side view thereof. The water pouch may be able to hold any suitable amount of water, for example 12 mL of water. As can be seen, the solid and broken lines in FIG. 14A indicate points of folding, temperature sealant, and sealing—used in developing an embodiment of the current invention (space was needed to fold and create an effective thermal seal).

Figure 16A:
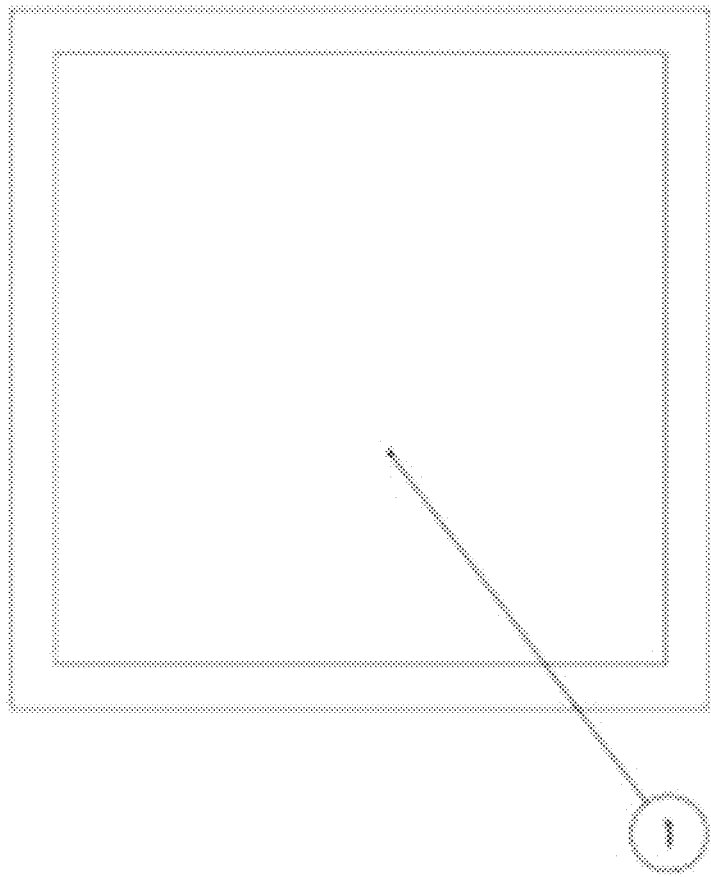
FIG. 16A is a schematic of a non-woven layer that can be disposed in the patch assembly of FIGS. 13A-13C.
Figure 16B:
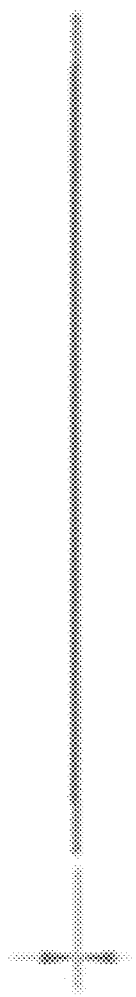
FIG. 16B is a side view of the non-woven layer of FIG. 16A.

Similarly, FIG. 15A is a schematic of the PCM pouches, FIG. 15B is a top view thereof, and FIG. 15C is a side view thereof. As can be seen, the solid and broken lines in FIG. 15A indicate points of folding and sealing—used in developing an embodiment of the current invention (space was needed to fold and create an effective thermal seal). FIGS. 16A-16B show the nonwoven layer component from the top/bottom and side, respectively. Numerical (1) refers to the nonwoven layer including CaO, as previously noted.

Figure 17A:
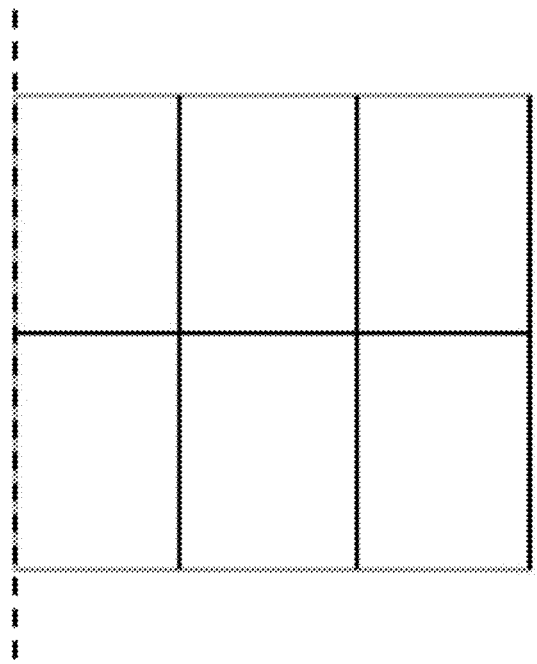
FIG. 17A is a schematic of a teabag (AAM) pouch that can be disposed in the patch assembly of FIGS. 13A-13C.
Figure 17B:
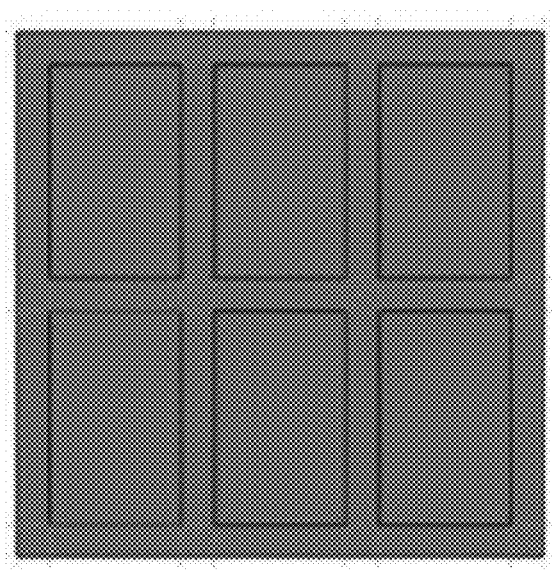
FIG. 17B is a top view of the teabag pouch of FIG. 17A.
Figure 17C:
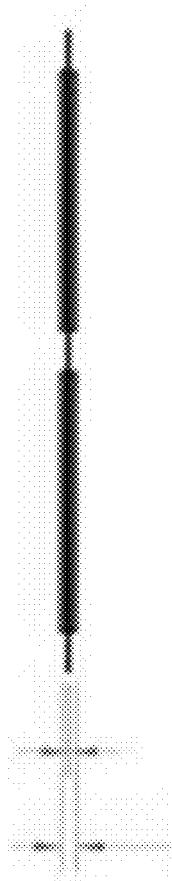
FIG. 17C is a side view of the teabag pouch of FIG. 17A.

FIG. 17A is a schematic of the teabag pouch, FIG. 17B is a top view thereof, and FIG. 17C is a side view thereof. As can be seen, the solid and broken lines in FIG. 17A indicate points of folding and sealing—used in developing an embodiment of the current invention (space was needed to fold and create an effective thermal seal).

Figure 18A:
FIG. 18A is a top view of an embodiment of the current invention.
Figure 18B:
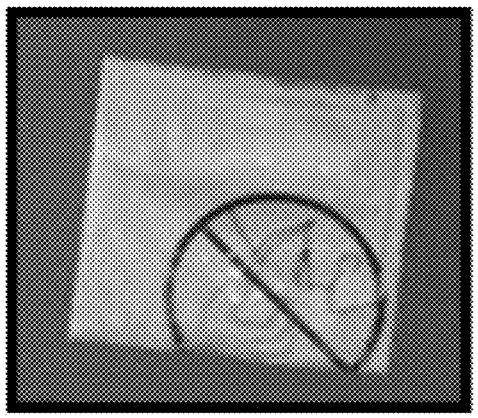
FIG. 18B depicts the water pouch of the embodiment of FIG. 18A.
Figure 18C:
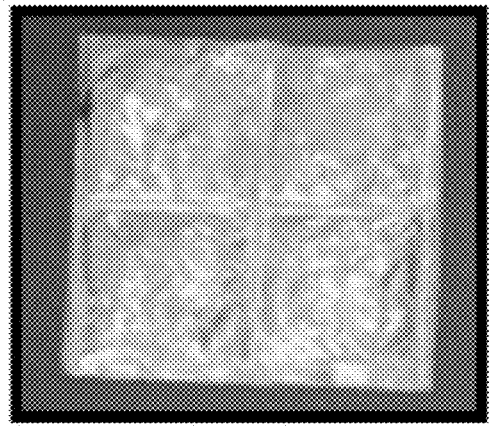
FIG. 18C depicts the PCM pouches of the embodiment of FIG. 18A.
Figure 18D:
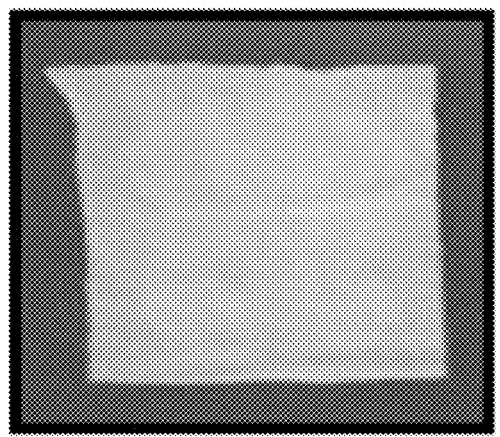
FIG. 18D depicts the nonwoven layer of the embodiment of FIG. 18A.
Figure 18E:
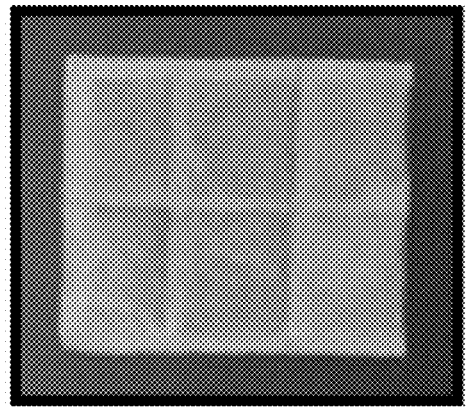
FIG. 18E depicts the teabag pouches of the embodiment of FIG. 18A.

FIGS. 18A-18E depict a prototype of the layered device and each layer thereof. FIG. 18A is an outer view of the device itself, showing the insulation (in red along the perimeter) and outer foil enclosure. FIG. 18B shows the water pouch, FIG. 18C shows the PCM pouch, FIG. 18D shows the nonwoven layer, and FIG. 18E shows the teabag pouch.

The reactions occurring inside of the teabag chemical pouch (AARM) within the layered device/patch include the following:

$$Mg+2H_2O \rightarrow Mg(OH)_2$$

$$CaO+H_2O \rightarrow Ca(OH)_2$$

$$Fe+3H_2O\ Fe_2O_3+H_2$$

A calorimeter was used to determine the conversion of each reaction. Since conversion was given in percentage, the formula below was used to find the concentration:

$$[A] = \frac{100}{100-x\ (\%)}$$

Figure 19:
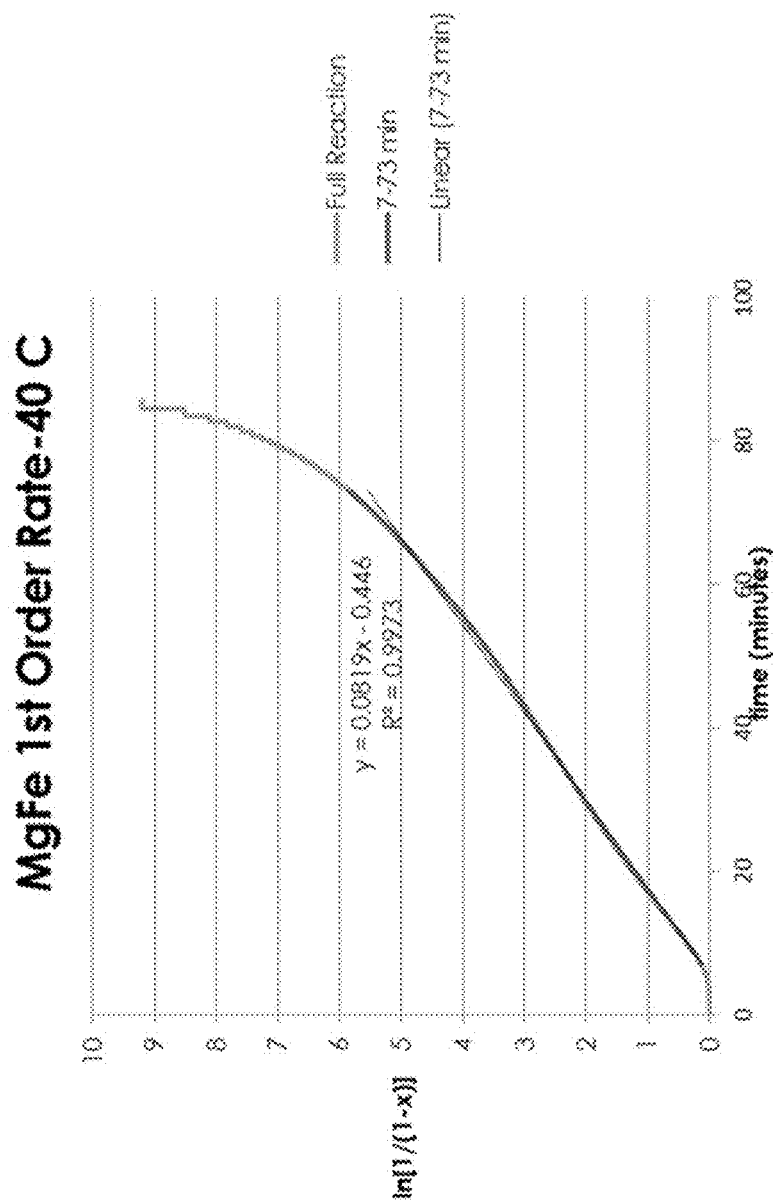
FIG. 19 is a graphical illustration showing rate of reaction for MgFe.
Figure 20:
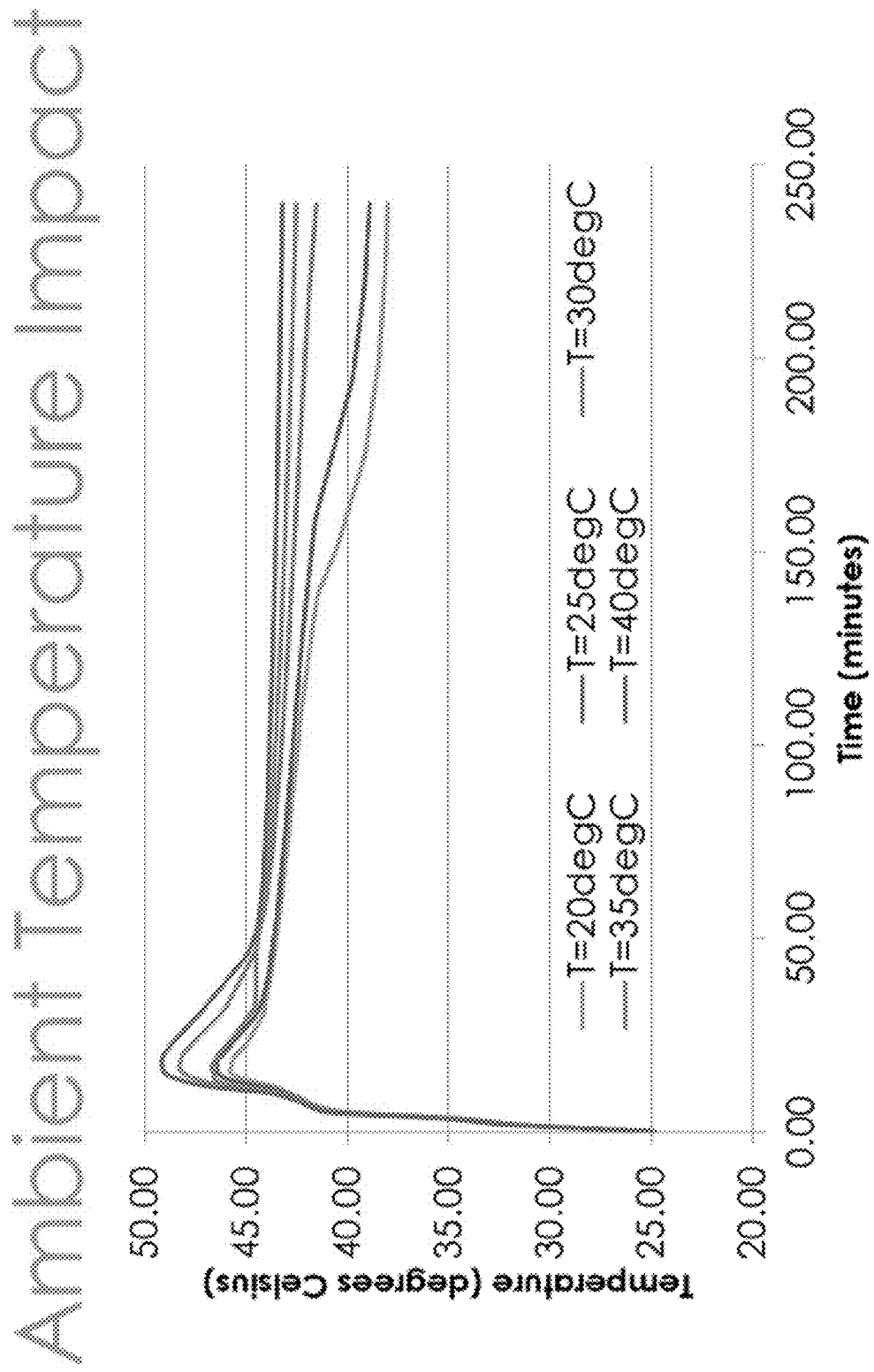
FIG. 20 is a graphical illustration showing effect of ambient temperature on a time-temperature model.
Figure 21:
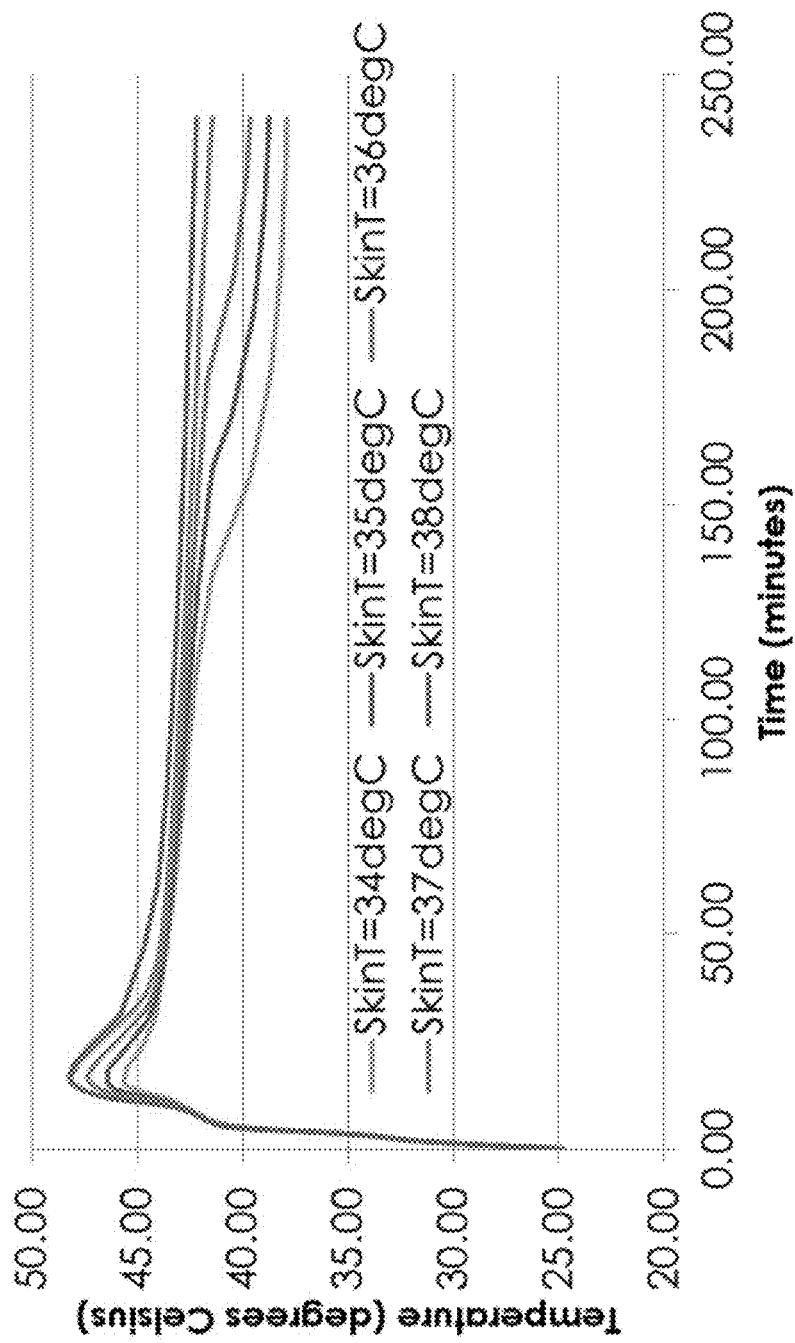
FIG. 21 is a graphical illustration showing effect of skin temperature on a time-temperature model.
Figure 22:
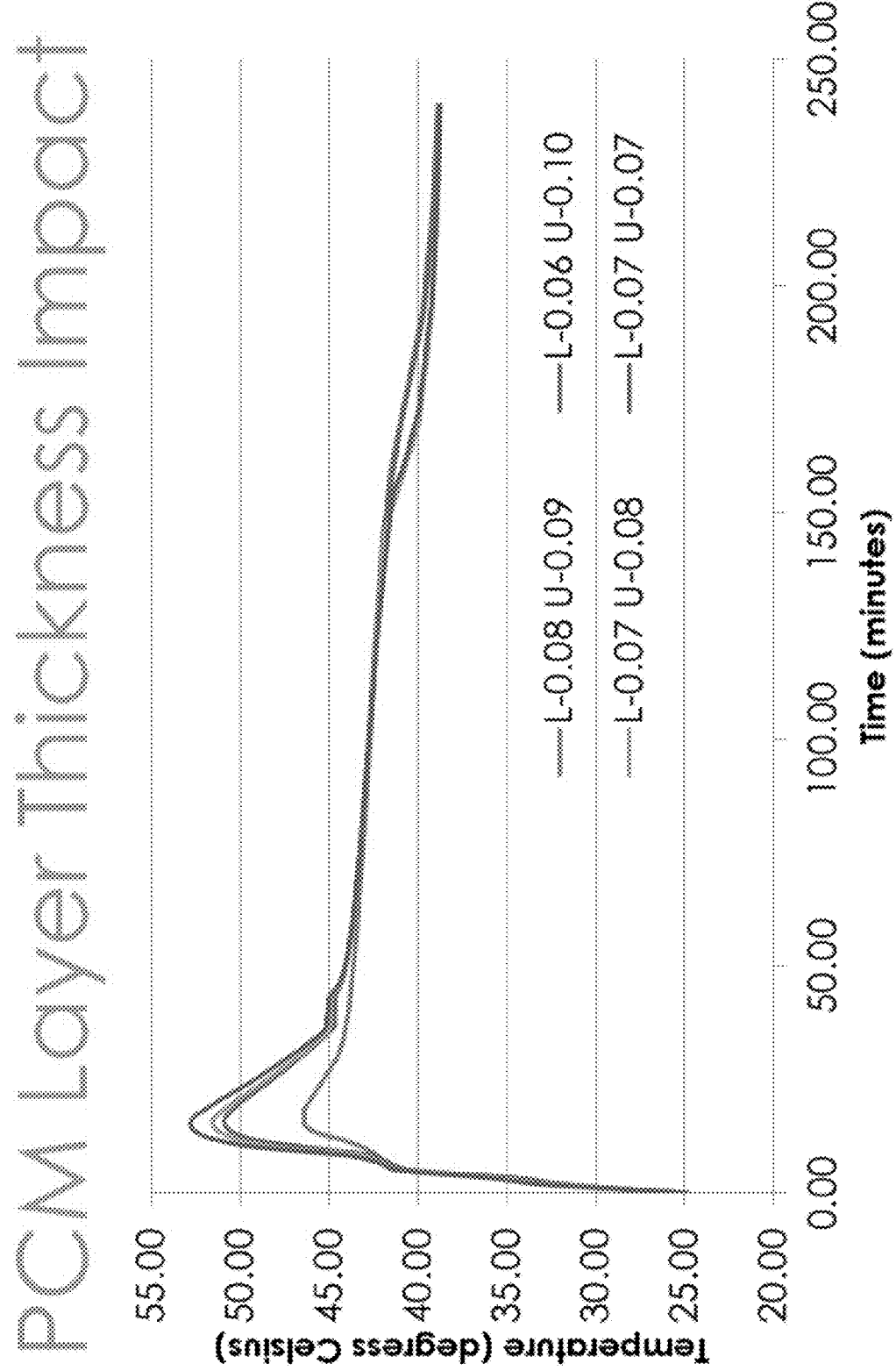
FIG. 22 is a graphical illustration showing effect of PCM layer thickness on a time-temperature model.
Figure 23:
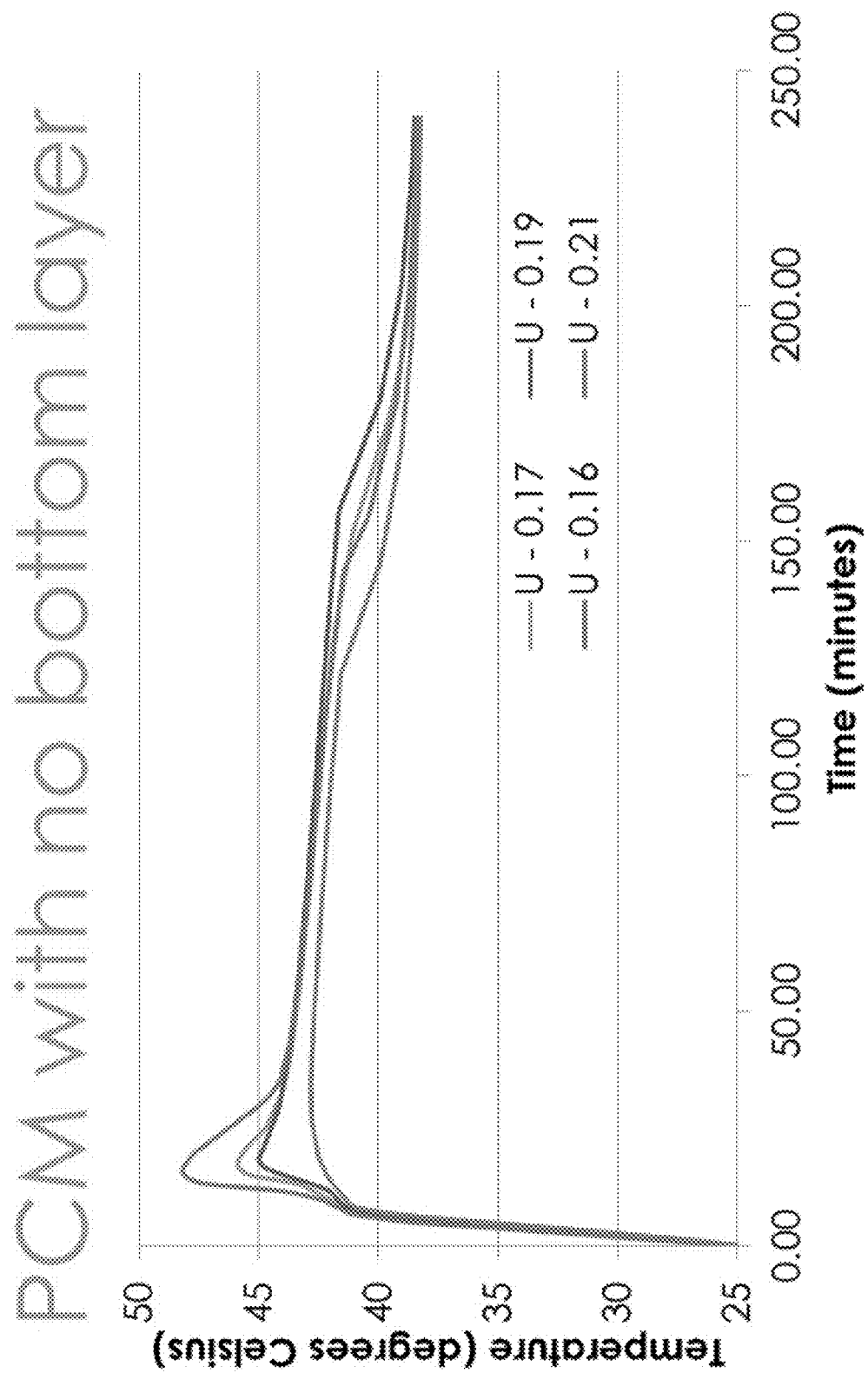
FIG. 23 is a graphical illustration showing effect of PCM with no bottom layer on a time-temperature model.
Figure 24:
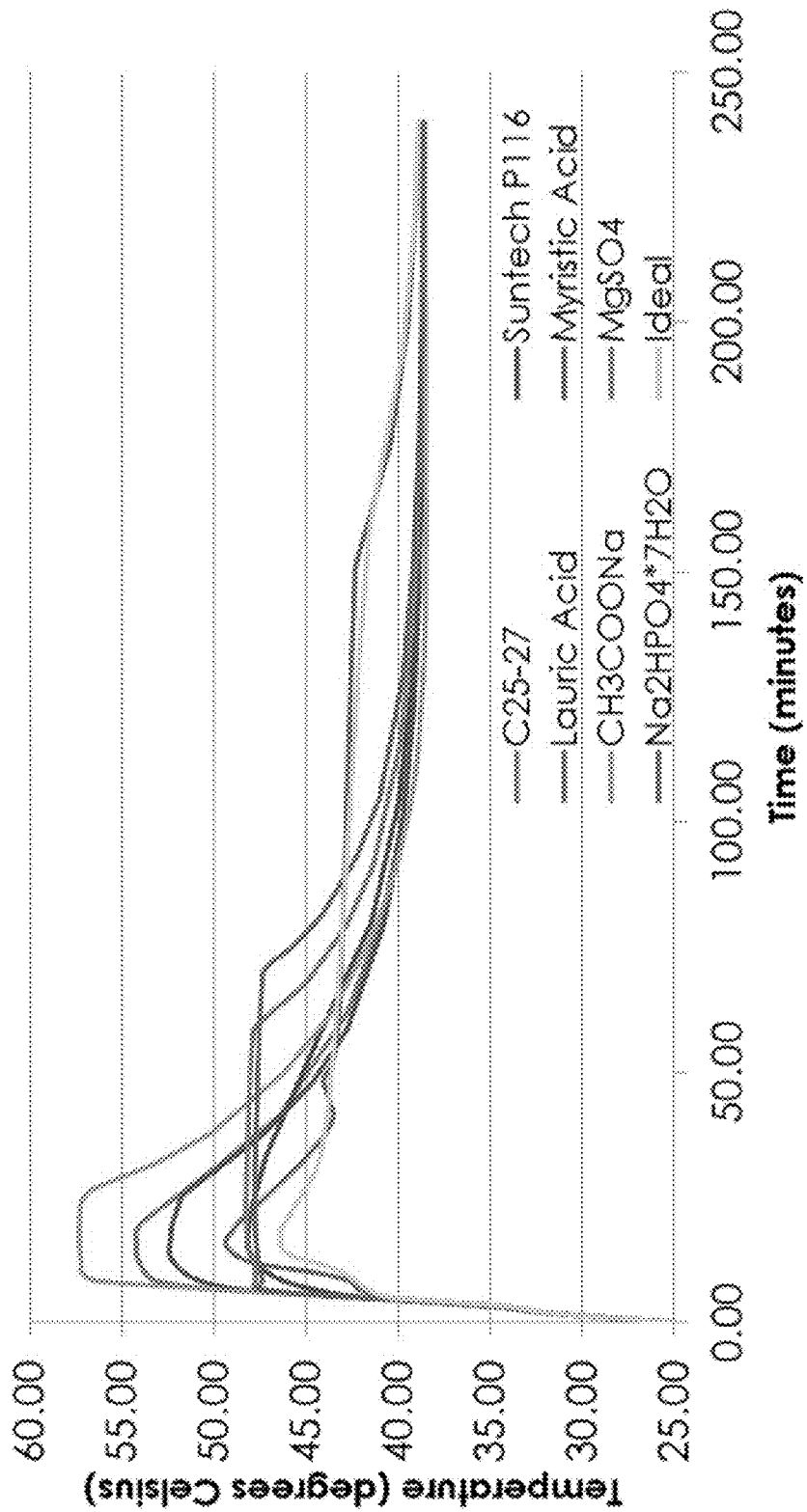
FIG. 24 is a graphical illustration showing effect of PCM materials on a time-temperature model.
Figure 25:
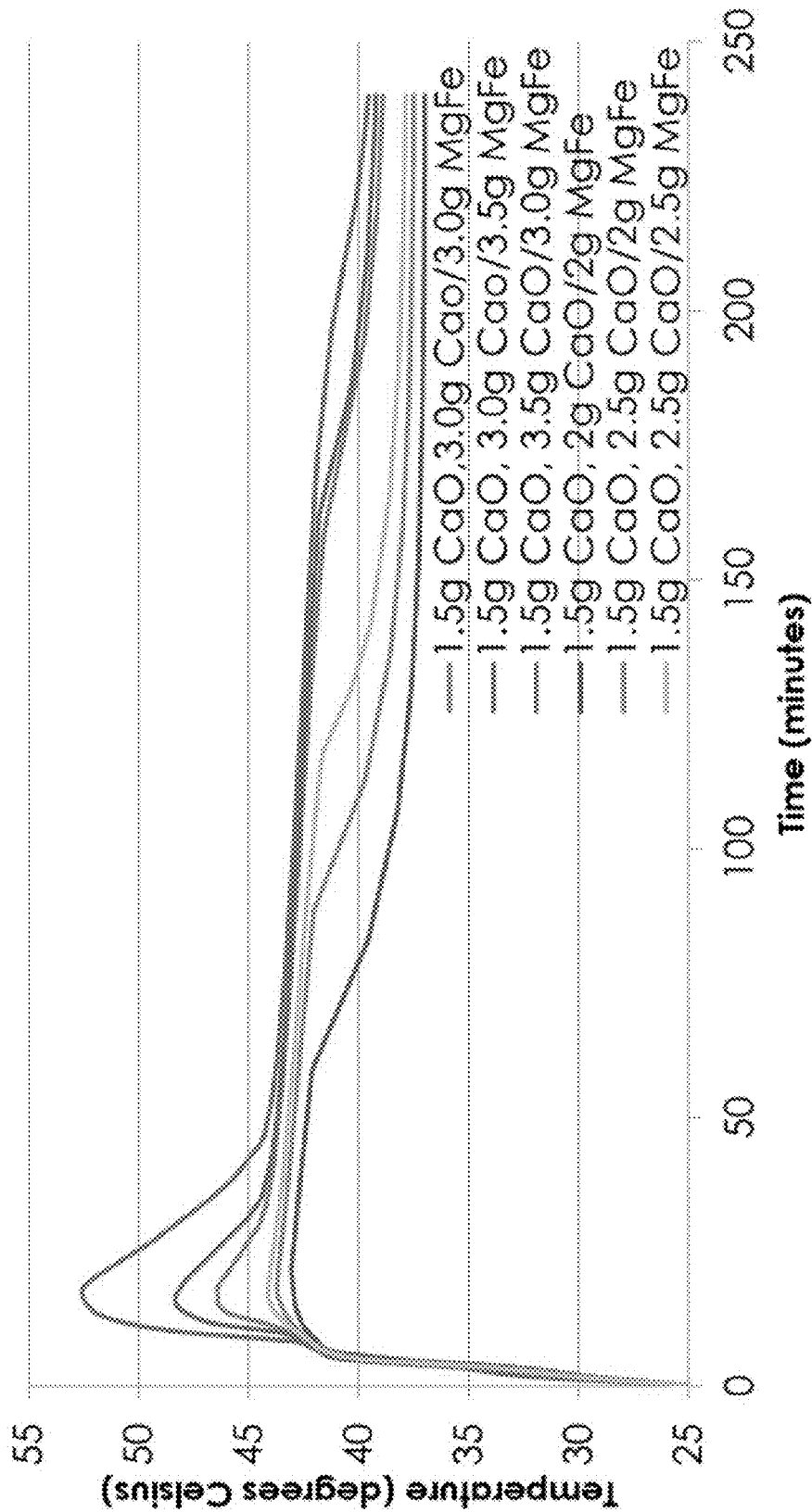
FIG. 25 is a graphical illustration showing effect of reaction mix on a time-temperature model.

The reaction kinetics of Ln[A] versus time for MgFe can be seen in FIG. 19, thus showing rate of reaction.

Once the rate of each reaction was found, COMSOL was used to model the reactions. The equation used to find the parameters used in COMSOL was the Arrhenius Equation:

$$k = Ae^{\frac{-E_a}{RT}}$$

The phase change material was tuned for latent heat of fusion and melting point range. Reaction heat modeling includes data from the calorimeter used to provide heat generation from individual reactions.

FIGS. 20-25 are graphical illustrations of time-temperature models based on the impact of different variables—ambient temperature, skin temperature, PCM layer thickness, PCM with no bottom layer, PCM materials, and reaction mix materials, respectively. Based on this model data, in an embodiment, the current invention includes a calcium oxide non-woven layer (about 1.5 g), a calcium oxide reaction mix (about 3 g), a magnesium iron reaction mix (about 3 g), a PCM amount in the upper layer of about 9 g, a PCM amount in the lower layer of about 8.0 g, and a preferred PCM of lauric acid (melting point 42-44° C., latent heat of fusion 178 kJ/kg).

Figure 26:
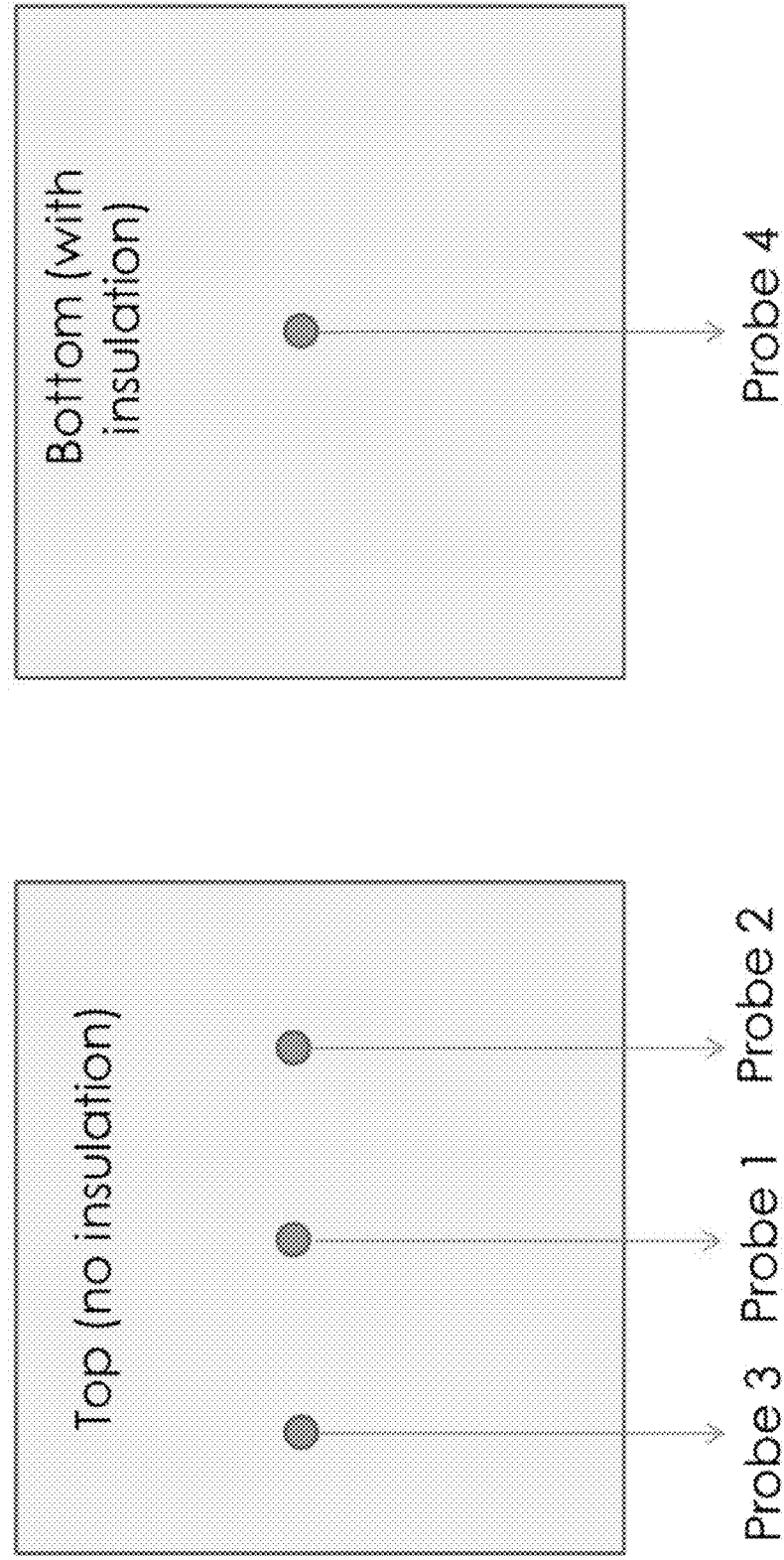
FIGS. 26A-26B depict exemplary placement of temperature probes in order to produce an accurate time-temperature profile of a particular patch.

The temperature profiles were generated for embodiments of the current invention in order to find the duration of the desired temperature and to optimize the patch. The temperature profiles were accomplished using LOGGERPRO and four (4) temperature probes, as seen in FIGS. 26A-26B.

Figure 27:
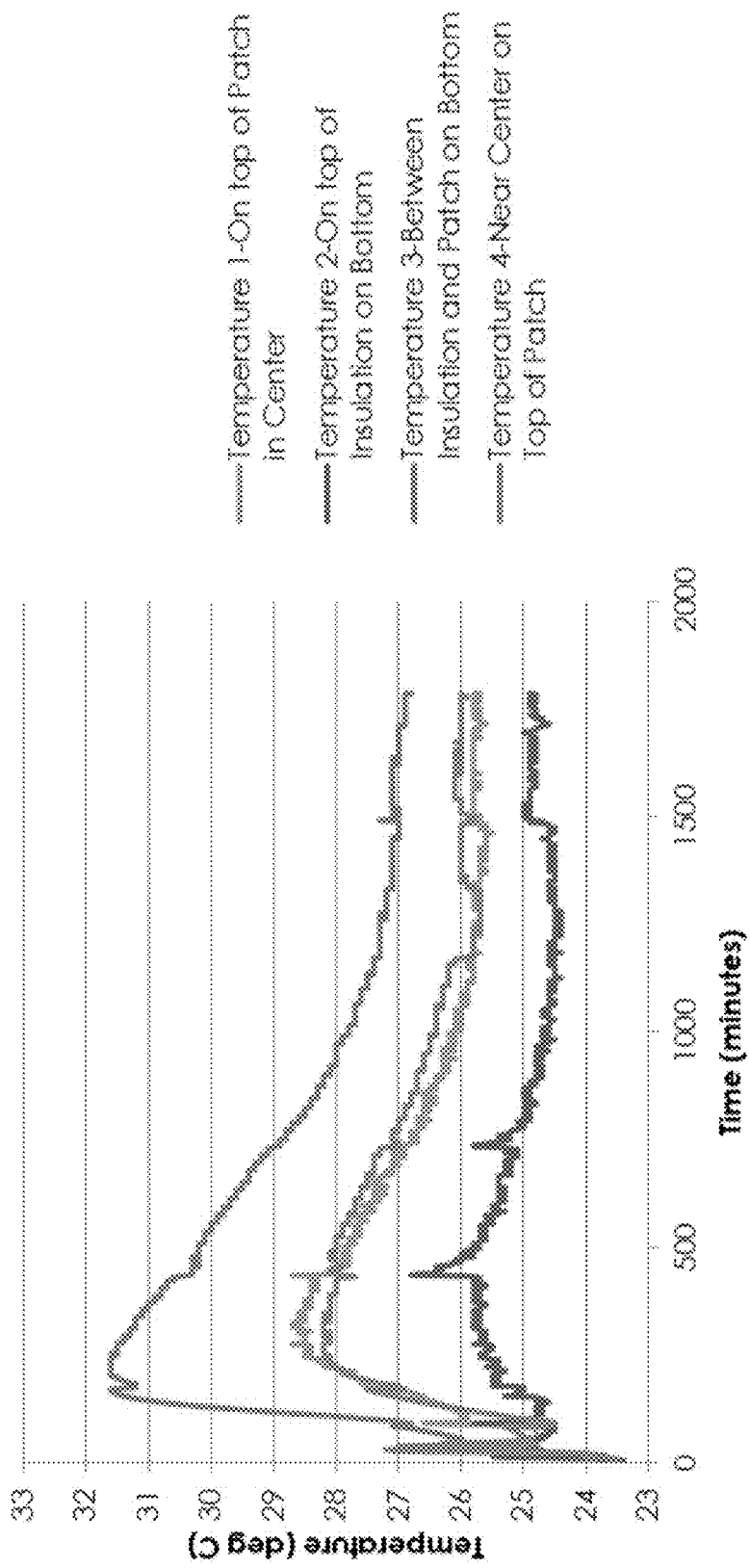
FIG. 27 is a graphical illustration of a time-temperature profile of a patch according to an embodiment of the current invention, where the patch has insulation only on the bottom.
Figure 28:
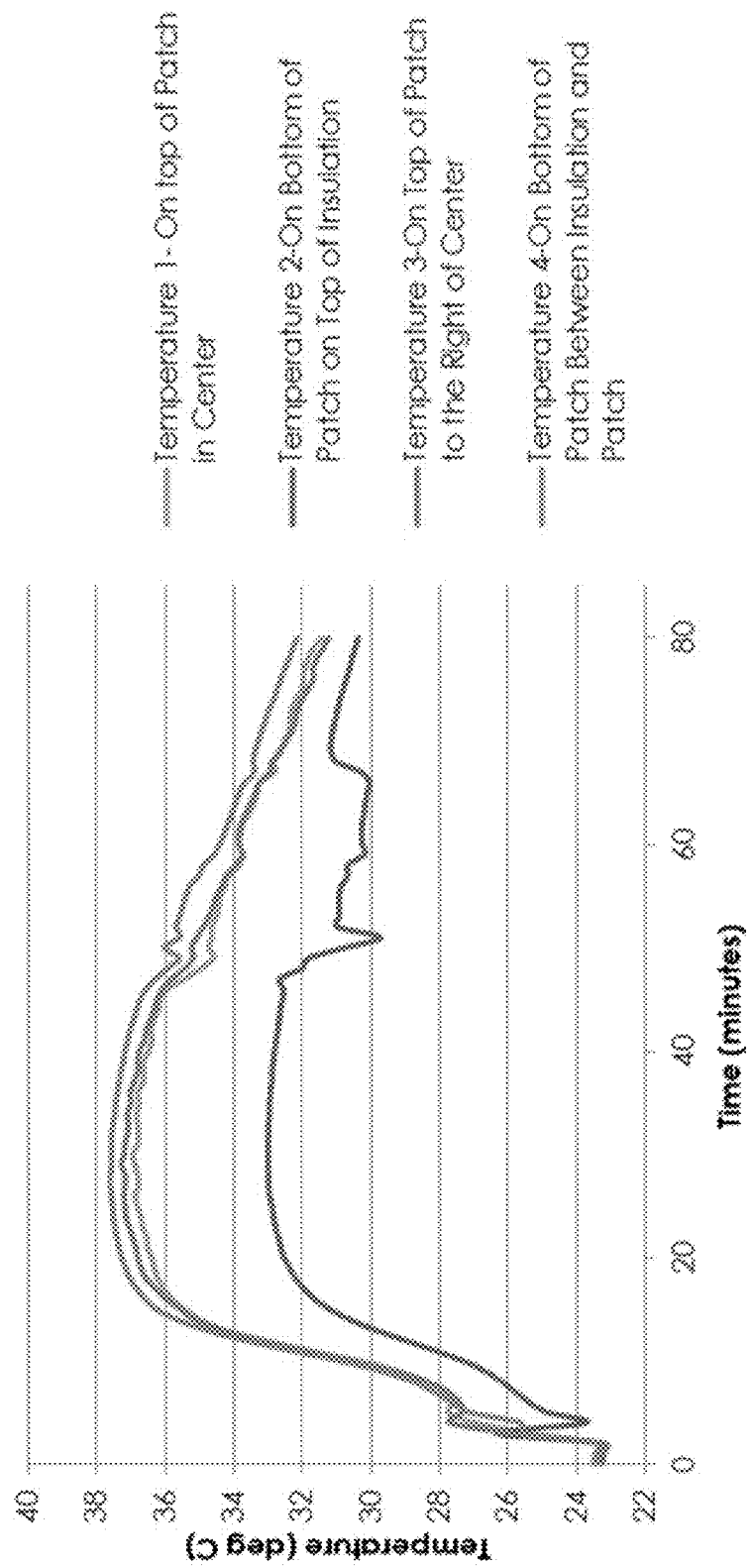
FIG. 28 is a graphical illustration of a time-temperature profile of a patch according to an embodiment of the current invention, where the patch includes a smaller water pouch.
Figure 29:
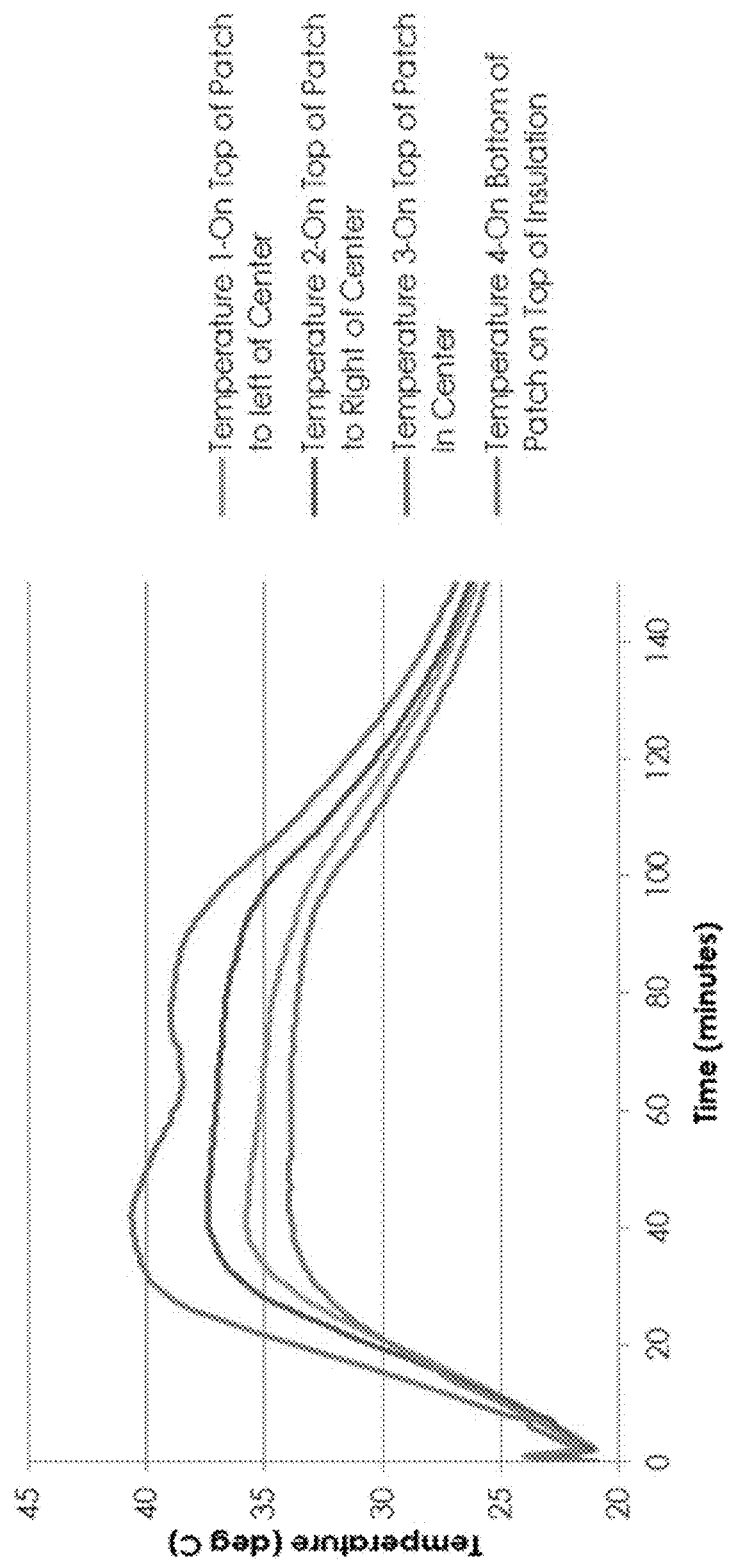
FIG. 29 is a graphical illustration of a time-temperature profile of a patch according to an embodiment of the current invention, where the patch is fully insulated.
Figure 30:
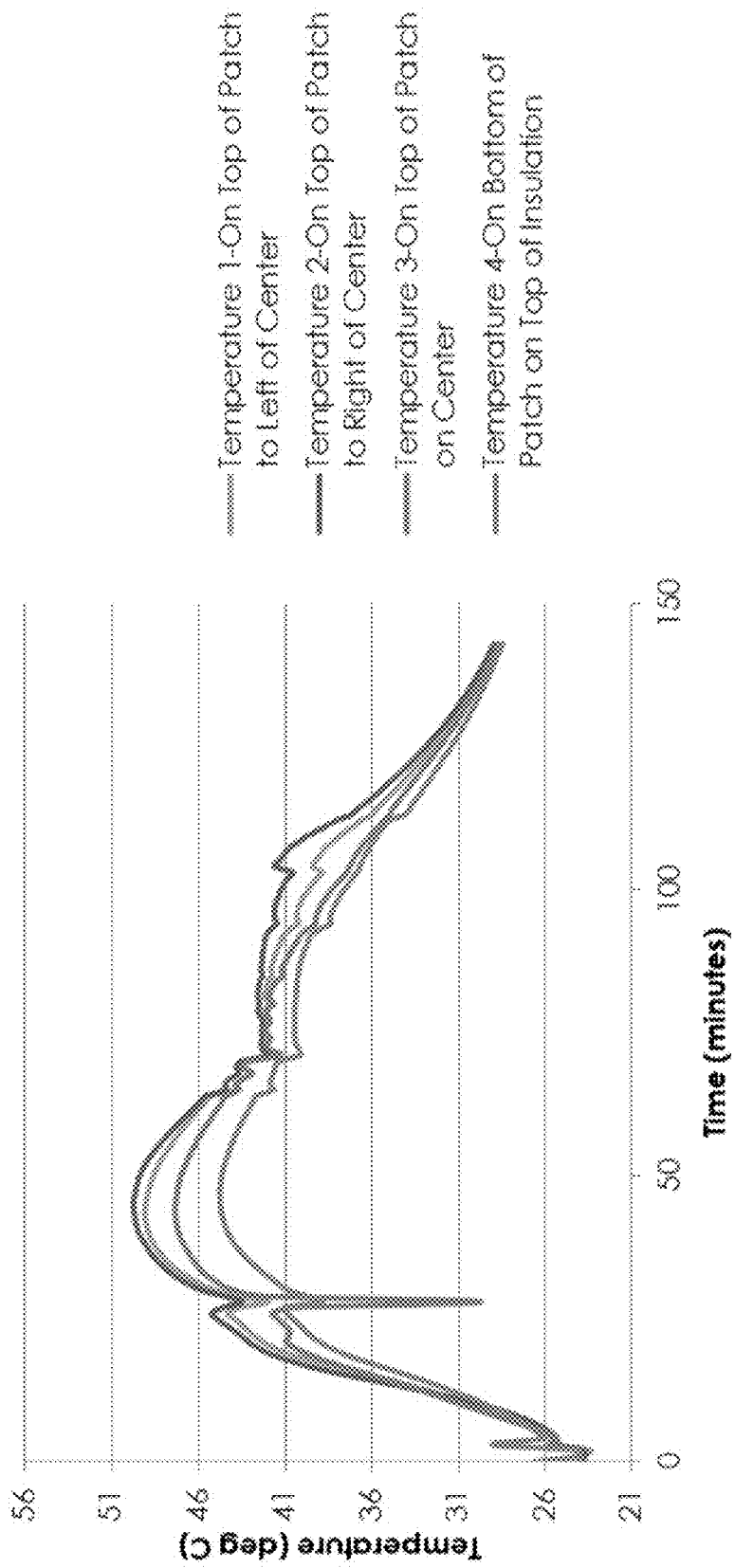
FIG. 30 is a graphical illustration of a time-temperature profile of a patch according to an embodiment of the current invention, where the patch includes more MgFe.

These time-temperature profiles can be seen in FIGS. 27-30. FIG. 27 shows an embodiment with insulation only on the bottom; FIG. 28 shows an embodiment of a smaller water pouch; FIG. 29 shows an embodiment with full insulation; and FIG. 30 shows an embodiment with more MgFe. The performance of these various configurations were exceptional, though unexpected, particularly with the PCM having a dual role as heat sink and heat source. The time profile of how much heat is absorbed and released is a key component in the current invention.

Regarding the amount of hydrogen produced, Meal, Ready-to-Eat (MRE) iron has a 1 to 1 ratio by weight. Three (3) g MRE in the patch equates to 1.5 g Mg. Considering the density of hydrogen gas at standard temperature and pressure is 89.9 g/m$^3$, the following provides the amount of hydrogen produced:

$$1.5 \text{ g Mg} * \frac{1 \text{ mol}}{24.3 \text{ g}} = 0.0617 \text{ mol Mg} = 0.0617 \text{ mol H}_2$$

$$0.0617 \text{ mol H}_2 * \frac{2.02 \text{ g}}{1 \text{ mol}} = 0.125 \text{ g H}_2$$

$$0.125 \text{ g H}_2 * \frac{1 \text{ m}^3}{89.9 \text{ g}} * \frac{1000 \text{ L}}{1 \text{ m}^3} * \frac{1000 \text{ mL}}{1 \text{ L}} = 1390 \text{ mL H}_2$$

In conclusion, both a CaO patch and a NaOAc/iron patch were fabricated for the demonstrated purposes. Regarding the CaO patch, the designated area was heated to the target temperature within about twenty (20) minutes, and the temperature was maintained for about ninety (90) minutes. Regarding the NaOAc/iron patch, the designated area was heated to the target temperature within about five (5) minutes to about (9) minutes, and the temperature was maintained for about 4.75 hours to about eight (8) hours.

Figure 31:
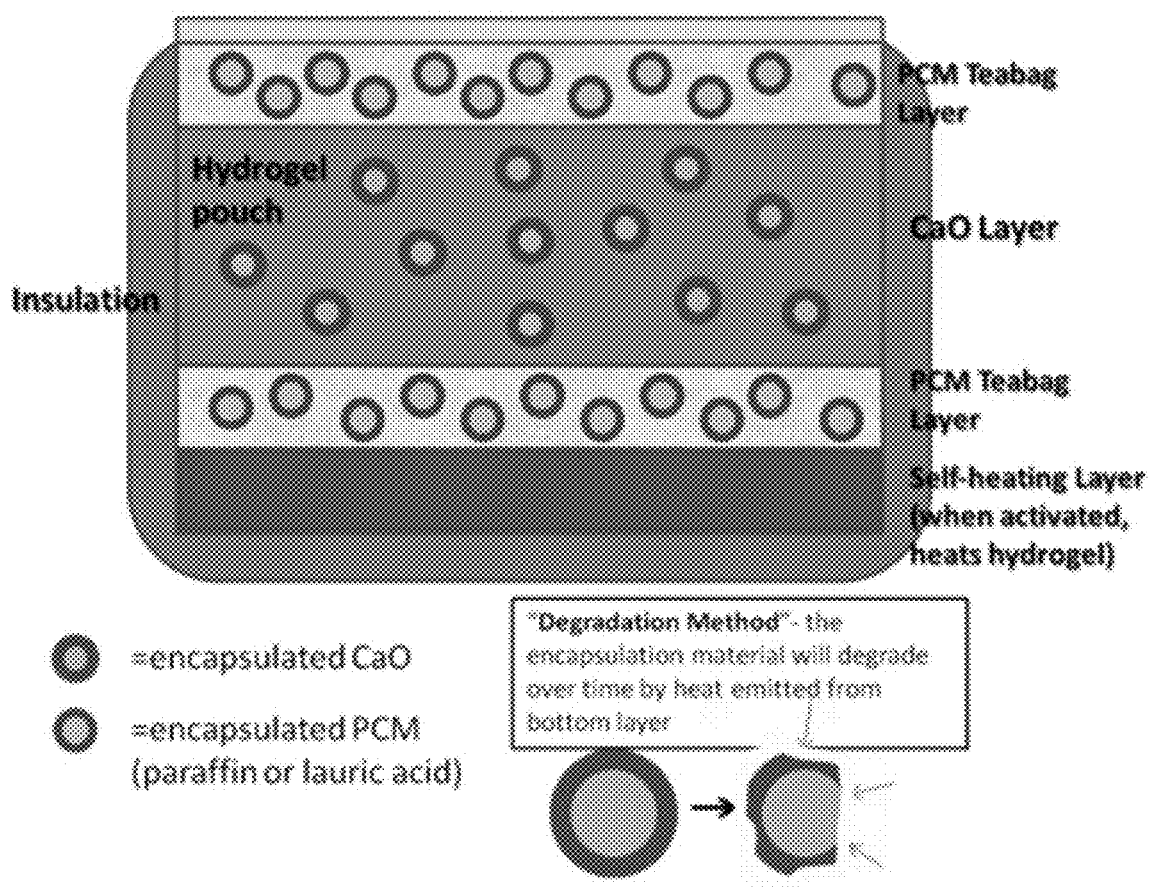
FIG. 31 is a schematic of an alternative embodiment of the current invention with encapsulations and hydrogel pouch.

An alternative embodiment of the current invention can be seen in FIG. 31 with encapsulated CaO, encapsulated PCM (e.g., paraffin, lauric acid), and hydrogel pouches.

Glossary of Claim Terms

Air-activated material: This term is used herein to refer to a substance that produces and releases heat when exposed to air/oxygen.

Contact surface: This term is used herein to refer to an external side that physically touches a body or mass with the goal of transferring heat to that body or mass. An example is a patch on a human body, where the patch heats up and releases heat into the body.

External environment: This term is used herein to refer to an area surrounding the current apparatus. This is typically air, or the interior of an object if the invention is contained within that object.

Insulation: This term is used herein to refer to a material used to reduce the flow of heating from one side of the insulation to the other side, and vice versa.

Phase change material: This term is used herein to refer to a substance that is capable of absorbing, storing, and releasing thermal energy. Typically, the substance undergoes a solid-liquid phase change (melting) when heat is absorbed and a liquid-solid phase change (freezing) when heat is released.

Sandwiching: This term is used herein to refer to positioning one layer between two other layers.

Substantially adjacent: This term is used herein to refer to a position of a component directly next to or very close to each other, where the components are nearly co-planar with one another. For example, a PCM layer can be directly abutting an AARM layer, or they may be separated from one another by just a thin nonwoven layer. In the latter case, they can still be considered "substantially" adjacent to one another.

Substantially around: This term is used herein to refer to a position of a component surrounding at least a majority of another component. Completely enclosing the other component is contemplated herein but not required. For example, FIGS. 6-8, 12, and 31 show insulation disposed "substantially around" the PCM and AAM layers, even though one side remains open and exposed to the external environment.

Thin nonwoven layer: This term is used herein to refer to a sheet or web structure bonded together by entangling fibers or filaments chemically, mechanically, thermally, or by solvent treatment. This layer is typically flat and porous can be formed of separate fibers or from molten polymer (e.g., molten plastic, plastic film, etc.). The porous nature of this layer may allow the AARM and PCM layers to transfer heat between each other, while also avoiding hotspots due to excessively rapid heating.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A self-heating, layered assembly having a top side, a bottom side, and a plurality of sidewalls, comprising:
a first layer including a phase change material;
a second layer including an air-activated material layered substantially adjacent to said first layer of said phase change material, said air-activated material activated by presence of oxygen, said air-activated material releasing heat upon activation,
said phase change material being a heat sink by absorbing heat released upon activation of said air-activated material, said phase change material being a heat source by slowly releasing said absorbed heat over time;
insulation disposed substantially around said first and second layers to modulate temperature and heat release over time; and
a top film forming said top side of said layered assembly above said first and second layers.

2. A self-heating, layered assembly as in claim 1, further comprising:
said bottom side of said layered assembly being a contact surface, said top side of said layered assembly being exposed to an external environment,
said first layer being disposed below said second layer, such that said air-activated material is exposed to said external environment.

3. A self-heating, layered assembly as in claim 1, further comprising:
said first layer being disposed below said second layer;
a third layer including additional air-activated material layered substantially adjacent to and below said first layer of said phase change material,
such that said air-activated material, said additional air-activated material, or both are exposed to said external environment.

4. A self-heating, layered assembly as in claim 1, further comprising:
said first layer being disposed above said second layer.

5. A self-heating, layered assembly as in claim 4, further comprising:
a third layer including additional phase change material layered substantially adjacent to and below said second layer of said air-activated material.

6. A self-heating, layered assembly as in claim 1, further comprising:
said phase change material including sodium acetate.

7. A self-heating, layered assembly as in claim 1, further comprising:
said air-activated material including an effective amount of one or more of calcium oxide, paraffin, a magnesium-iron mix, and zeolite.

8. A self-heating, layered assembly as in claim 1, further comprising:
a thin nonwoven layer disposed between said air-activated material and said phase change material, said nonwoven layer including calcium oxide.

9. A self-heating, layered assembly as in claim 1, further comprising:
a water pouch disposed above said first layer and said second layer, said water pouch forming at least a portion of said top side of said layered assembly.

10. A self-heating, layered assembly as in claim 1, further comprising:
said first layer including at least four (4) pouches of said phase change material.

11. A self-heating, layered assembly as in claim 10, further comprising:
said second layer including at least six (6) pouches of said air-activated material.

12. A self-heating, layered assembly as in claim 1, further comprising:
said layered assembly configured to reach a temperature of over about 40° C. within about thirty (30) seconds of activation of said air-activated materials.

13. A self-heating, layered assembly as in claim 12, further comprising:
said phase change material releasing heat for over about six (6) hours while maintaining said temperature over about 40° C.

14. A self-heating, layered assembly as in claim 1, further comprising:
said phase change material being encapsulated, and
at least a portion of said air-activated material being encapsulated.

15. A self-heating, layered assembly having a top side, a bottom side, and a plurality of sidewalls, comprising:
a bottom layer formed of phase change material, said phase change material including sodium acetate;
a top layer formed of air-activated reactive material and disposed adjacent to said bottom layer, said air-activated material including zeolite, calcium oxide, a mixture of magnesium and iron, and paraffin, said bottom layer being disposed below said top layer,
said air-activated material activated by presence of oxygen, said air-activated material releasing heat upon activation,
said phase change material being a heat sink by absorbing heat released upon activation of said air-activated material, said phase change material being a heat source by slowly releasing said absorbed heat over time,
said bottom side of said layered assembly being a contact surface, said top side of said layered assembly being exposed to an external environment;
a third layer including additional air-activated material layered substantially adjacent to and below said bottom layer of said phase change material,
such that said air-activated material, said additional air-activated material, or both are exposed to said external environment;
a top film forming said top side of said layered assembly above said first top and bottom layers;
insulation disposed substantially around said bottom layer and said top layer,
said layered assembly configured to reach a temperature of over about 40° C. within about thirty (30) seconds of activation of said air-activated materials, said phase change material releasing heat for over about six (6) hours while maintaining said temperature over about 40° C.

16. A method of manufacturing a self-heating, layered assembly for customizing a time-temperature profile for said layered assembly, wherein said layered assembly has a top side, a bottom side, and a plurality of sidewalls, the method comprising:
providing a first layer including phase change material;
providing a second layer including air-activated material, said air-activated material activated by presence of oxygen, said air-activated material releasing heat upon activation,
said phase change material being a heat sink by absorbing heat released upon activation of said air-activated material, said phase change material being a heat source by slowly releasing said absorbed heat over time;

layering said first layer and said second layer on one another within said layered assembly;

positioning said second layer above or below said first layer depending on access of said top side and said bottom side to an external environment;

disposing insulation substantially around said first and second layers to modulate temperature and heat release over time; and disposing a film substantially adjacent to said second layer to provide a barrier between said second layer and said external environment.

17. A method as in claim 16, further comprising:

sandwiching said second layer between said first layer and a third layer that includes additional phase change material.

18. A method as in claim 16, further comprising:

sandwiching said first layer between said second layer and a third layer that includes additional air-activated material.

19. A method as in claim 16, further comprising:

disposing a thin nonwoven layer between said air-activated material and said phase change material, said nonwoven layer including calcium oxide.

20. A method as in claim 16, further comprising:

positioning a water pouch above said first layer and said second layer, said water pouch forming at least a portion of said top side of said layered assembly.

21. A self-heating, layered assembly as in claim 16, further comprising:

said layered assembly configured to reach a temperature of over about 40° C. within about thirty (30) seconds of activation of said air-activated materials.

22. A self-heating, layered assembly as in claim 21, further comprising:

said phase change material releasing heat for over about six (6) hours while maintaining said temperature over about 40° C.

23. A self-heating, layered assembly as in claim 16, further comprising:

encapsulating said phase change material, and encapsulating at least a portion of said air-activated material.

* * * * *

UNITED STATES PATENT AND TRADEMARK OFFICE
CERTIFICATE OF CORRECTION

| | | |
|---|---|---|
| PATENT NO. | : 9,863,687 B1 | Page 1 of 1 |
| APPLICATION NO. | : 14/826416 | |
| DATED | : January 9, 2018 | |
| INVENTOR(S) | : Aydin K. Sunol et al. | |

It is certified that error appears in the above-identified patent and that said Letters Patent is hereby corrected as shown below:

In the Claims

Column 16, Claim 15, Line 45 should read:
above said top and bottom layers;

Signed and Sealed this
Twelfth Day of June, 2018

Andrei Iancu
*Director of the United States Patent and Trademark Office*